(12) United States Patent
Blackwell et al.

(10) Patent No.: US 12,070,445 B2
(45) Date of Patent: Aug. 27, 2024

(54) SYSTEM AND ASSAY FOR MONITORING PRODUCTION/RELEASE OF MEMBRANE-LYTIC TOXINS IN BACTERIA AND COMPOUNDS FOR MODULATING SAME

(71) Applicant: Wisconsin Alumni Research Foundation, Madison, WI (US)

(72) Inventors: Helen Elizabeth Blackwell, Middleton, WI (US); Thomas John Polaske, Madison, WI (US); David Lynn, Middleton, WI (US); Curran Gahan, Madison, WI (US); Kayleigh E. Nyffeler Bucci, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 0 days.

(21) Appl. No.: 17/896,558

(22) Filed: Aug. 26, 2022

(65) Prior Publication Data

US 2023/0070337 A1 Mar. 9, 2023

Related U.S. Application Data

(60) Provisional application No. 63/237,986, filed on Aug. 27, 2021.

(51) Int. Cl.
*A61K 31/381* (2006.01)
*A61P 31/04* (2006.01)

(52) U.S. Cl.
CPC ............ *A61K 31/381* (2013.01); *A61P 31/04* (2018.01)

(58) Field of Classification Search
CPC .................................................. A61K 31/381
See application file for complete search history.

(56) References Cited

U.S. PATENT DOCUMENTS

2012/0232035 A1\* 9/2012 Jones ....................... A61P 31/12
514/233.2
2021/0040098 A1\* 2/2021 Smith ...................... A61P 25/00

FOREIGN PATENT DOCUMENTS

WO WO-2019/032720 A1 2/2019

OTHER PUBLICATIONS

Boursier, et al. "Structure function analyses of the N-butanoyl L-homoserine lactone quorum-sensing signal define features critical to activity in RhlR", (2018) ACS Chem. Biol., 13:2655-2662.
Brewster, J. D. "A simple micro-growth assay for enumerating bacteria," (2003) J. Microbiol. Methods, 53:77-86.
De Kievit, et al., "Quorum-sensing genes in Pseudomonas aeruginosa biofilms: their role and expression patterns," (2001) Appl. Environ. Microbiol. 67(4):1865-1873.
Eibergen, et al. "Potent and selective modulation of the RhlR quorum sensing receptor by using non-native ligands: An emerging target for virulence control in Pseudomonas aeruginosa," (2015) ChemBioChem, 16:2348-2356.
Gerdt, et al., "Competition studies confirm two major barriers that can preclude the spread of resistance to quorum-sensing inhibitors in bacteria," (2014) ACS Chem. Biol., 9:2291-2299.
Hodgkinson, et al. "Robust routes for the synthesis of N-acylated-Lhomoserine lactone (AHL) quorum sensing molecules with high levels of enantiomeric purity," (2011) Tet. Lett., 52:3291-3294.
Kirchdoerfer, et al., "Structural basis for ligand recognition and discrimination of a quorum-quenching antibody" (2011) J. Biol. Chem., 286(19):17351-17358.
Laabei, et al., "*Staphylococcus aureus* interaction with phospholipid vesicles—a new method to accurately determine accessory gene regulator (agr) activity," (2014) PLoS One, 9(1):e87270, 12 pages.
Laabei, et al., "A new assay for rhamnolipid detection-important virulence factors of Pseudomonas aeruginosa," (2014) Appl. Microbiol. Biotechnol., 98(1):7199-7209.
Lapinski, et al., "Comparison of liposomes formed by sonication and extrusion: Rotational and translational diffusion of an embedded chromophore," (2007) Langmuir, 23(23):11677-11683.
Lyon, et al., "Rational design of a global inhibitor of the virulence response in *Staphylococcus aureus*, based in part on localization of the site of inhibition to the receptor-histidine kinase," (2000) AgrC. Proc. Natl. Acad. Sci. U.S.A., 97(24):13330-13335.
Manson, et al., "Design, synthesis, and biochemical characterization of non-native antagonists of the Pseudomonas aeruginosa quorum sensing receptor LasR with nanomolar IC50 values," (2020) ACS Infect. Dis., 6:649-661.
Mayer, et al., "Vesicles of variable sizes produced by a rapid extrusion procedure," (1986) Biochim. Biophys. Acta, 858:161-168.
Muh, et al., "Novel Pseudomonas aeruginosa quorum-sensing inhibitors identified in an ultra-highthroughput screen," (2006) Antimicrob. Agents Chemother., 50(10):3674-3679.
Novick, et al., "Synthesis of Staphylococcal virulence factors is controlled by a regulator RNA molecule," EMBO J. (1993) 12(10):3967-3975.
Novick, R. P., "Properties of a cryptic high-frequency transducing phage in *Staphylococcus aureus*," (1967) Virology 33:155-166.
Novick, R. P., "Autoinduction and signal transduction in the regulation of staphylococcal virulence," (2003) Mol. Microbiol., 48(6):1429-1449.

(Continued)

*Primary Examiner* — Paul V Ward
(74) *Attorney, Agent, or Firm* — Foley & Lardner LLP

(57) ABSTRACT

The present technology provides a system for monitoring quorum-sensing in bacteria comprising bacteria that release at least one membrane-lytic toxin when the bacteria are at a quorum-sensing density; synthetic lipid vesicles comprising an environmentally sensitive indicator, wherein the synthetic lipid vesicles release the environmentally sensitive dye in the presence of an effective amount of the membrane-lytic toxins; and a growth medium; wherein the bacteria and synthetic lipid vesicles are in contact with the growth medium. Methods using the system and compounds discovered with the system (e.g., compounds of Formulas I and II) are also disclosed.

14 Claims, 12 Drawing Sheets

(56) References Cited

OTHER PUBLICATIONS

Schuster, et al., "Identification, timing, and signal specificity of Pseudomonas aeruginosa quorum-controlled genes: A transcriptome analysis," (2003) J. Bacteriol., 185:2066-2079.

Schuster, et al., "LuxR-type proteins in Pseudomonas aeruginosa quorum sensing: Distinct mechanisms with global implications," (2008) Chemical communication among bacteria. Washington, DC: ASM Press. pp. 133-144.

Starkey, et al., "Identification of anti-virulence compounds that disrupt quorum-sensing regulated acute and persistent pathogenicity" (2014) PLoS Pathog., 10(8):e1004321, 17 pages.

Sully, et al., "Selective chemical inhibition of agr quorum sensing in Staphylococcus aureus promotes host defense with minimal impact on resistance," (2014) PLoS Pathog., 10(6): e1004174, 14 pages.

Tal-Gan, et al. "Highly stable, midebridged autoinducing peptide analogues that strongly inhibit the AgrC quorum sensing receptor in Staphylococcus aureus," (2016) Angew. Chem. Int. Ed., 55:8913-8917.

Tal-Gan, et al., "Highly potent inhibitors of quorum sensing in Staphylococcus aureus revealed through a systematic synthetic study of the group-III autoinducing peptide," (2013) J. Am. Chem. Soc. 135:7869-7882.

Thet, et al., "Visible, colorimetric dissemination between pathogenic strains of Staphylococcus aureus and 31 Pseudomonas aeruginosa using fluorescent dye containing lipid vesicles," (2013) Biosens. Bioelectron., 41:538-543.

Vasquez, et al., "Simplified autoinducing peptide mimetics with single nanomolar activity against the Staphylococcus aureus AgrC quorum sensing receptor," (2019) ACS Infect. Dis., 5:484-492.

Welsh, et al., "Chemical genetics reveals environment-specific roles for quorum sensing circuits in Pseudomonas aeruginosa," (2016) Cell Chem. Biol., 23(3):361-369.

Welsh, et al., "Small molecule disruption of quorum sensing cross-regulation in Pseudomonas aeruginosa causes major and unexpected alterations to virulence phenotypes," (2015) J. Am. Chem. Soc., 137:1510-1519.

Yarwood, et al., "Quorum sensing in Staphylococcus aureus biofilms" (2004) J. Bacteriol., 186(6):1838-1850.

\* cited by examiner

FIGS. 1A–1C
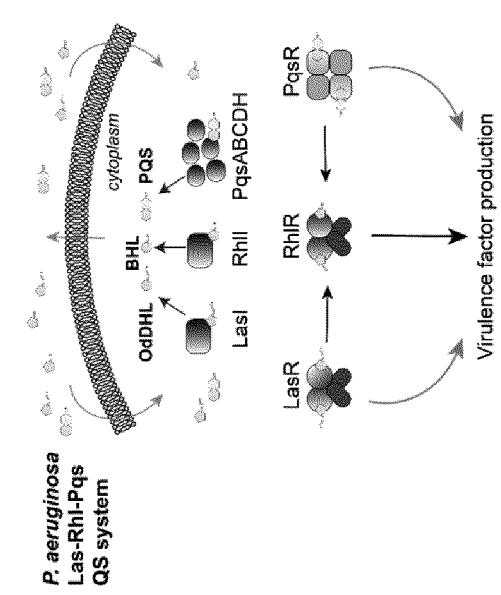
FIG. 1A *S. aureus agr* QS system
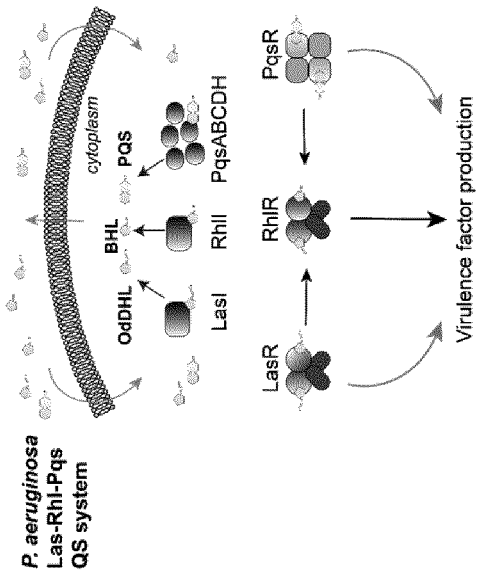
FIG. 1B *P. aeruginosa* Las-Rhl-Pqs QS system
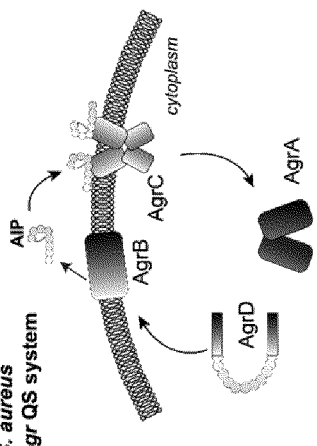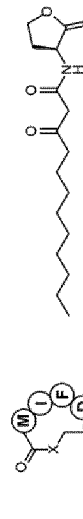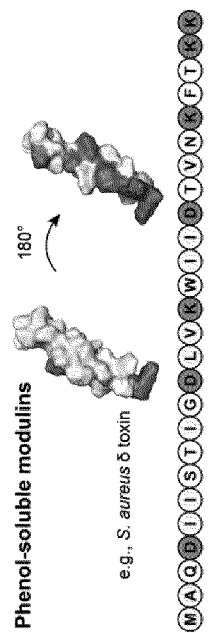
FIG. 1C

FIGS. 2A – 2D
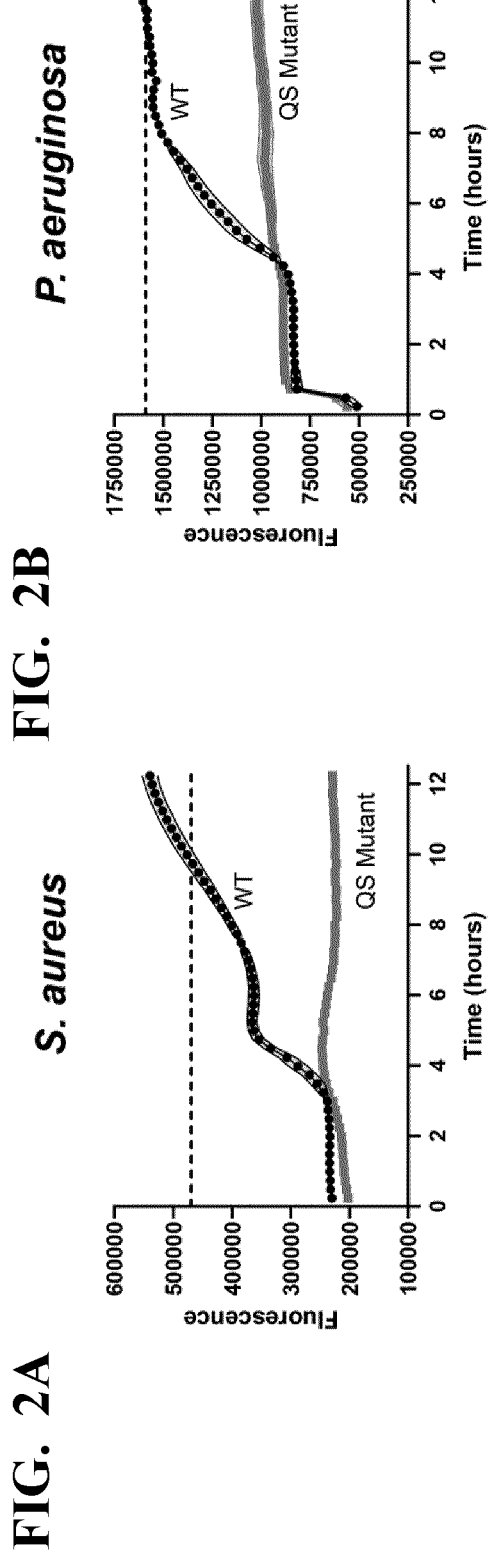
FIG. 2A
FIG. 2C
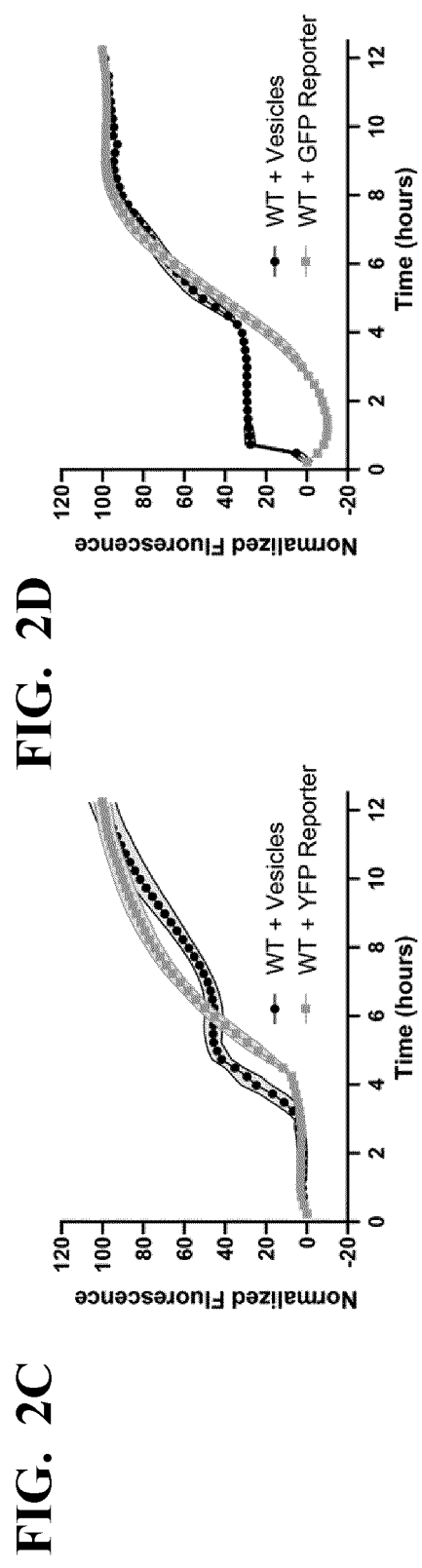
FIG. 2B
FIG. 2D

FIGS. 3A – 3C
FIG. 3A
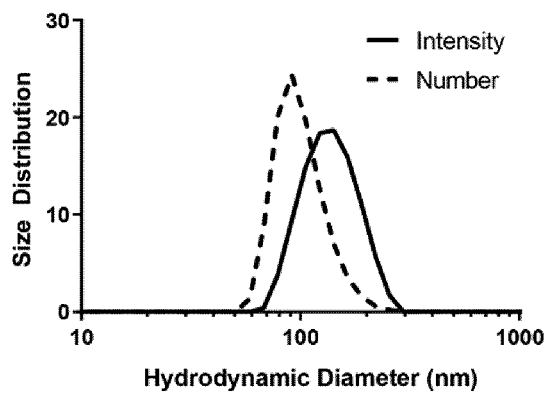
FIG. 3B
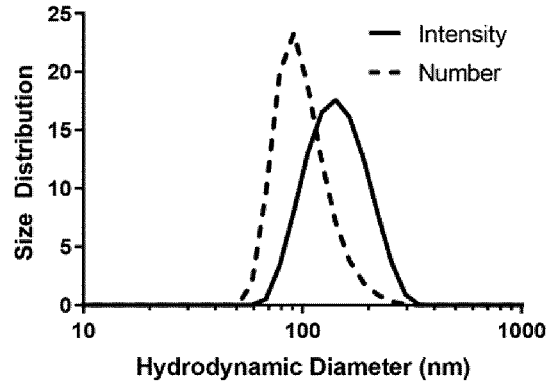
FIG. 3C
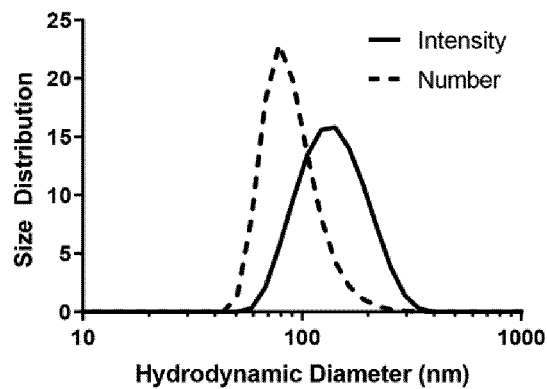

FIGS. 4A – 4D
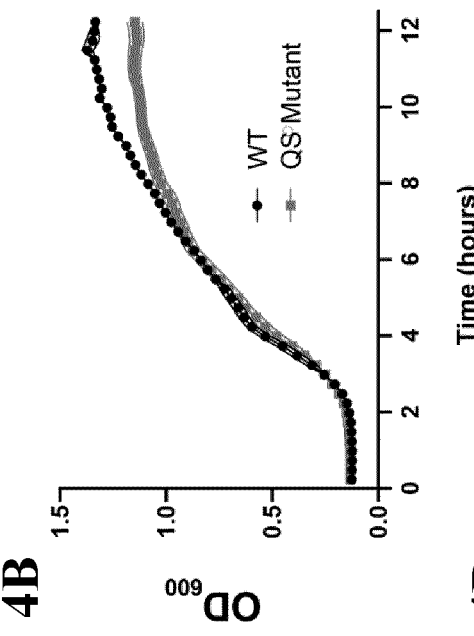
FIG. 4B
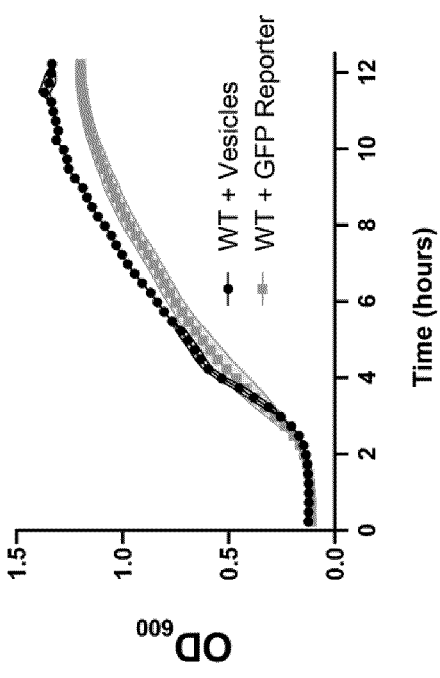
FIG. 4D
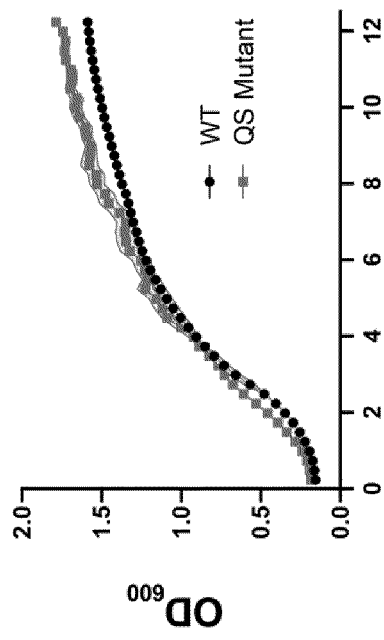
FIG. 4A
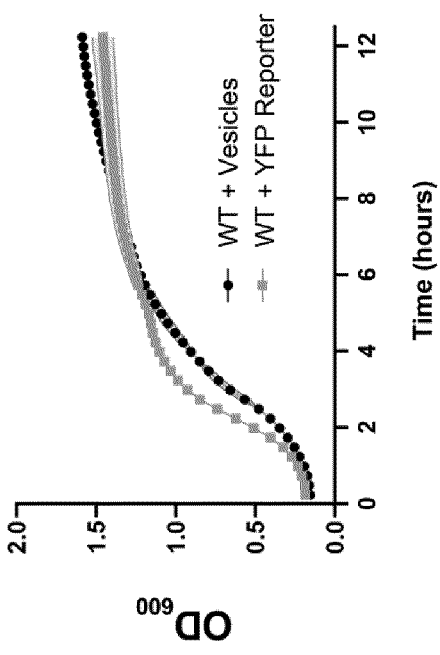
FIG. 4C

FIGS. 5A – 5B
FIG. 5A
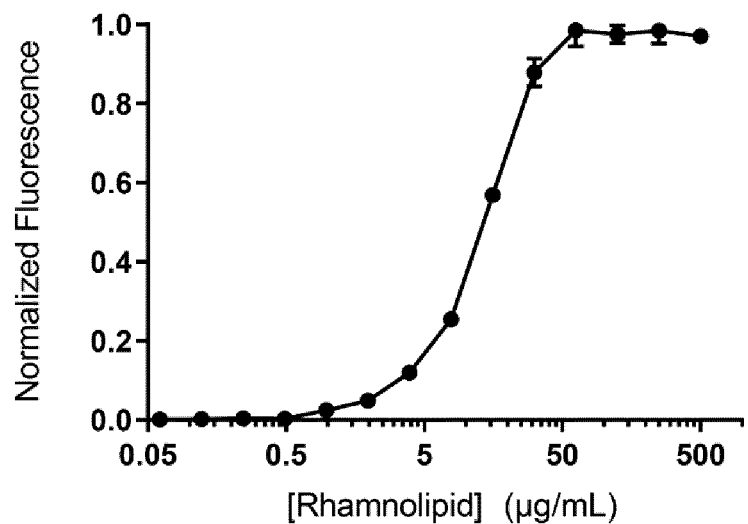
FIG. 5B
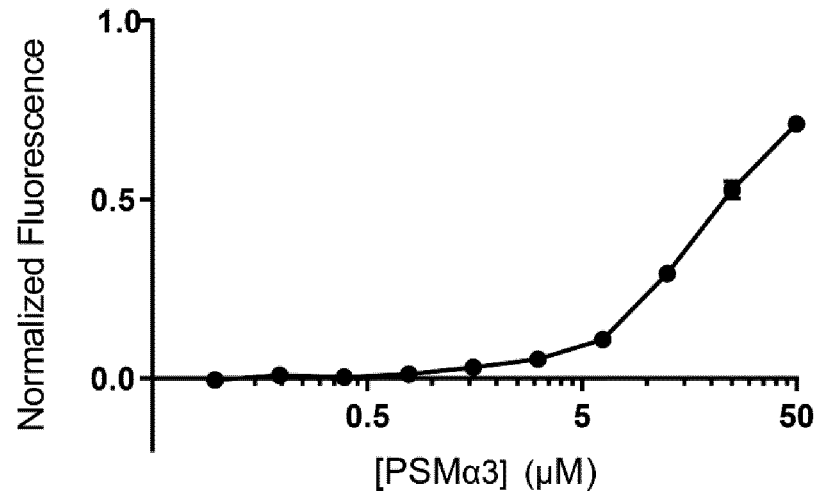

FIGS. 6A – 6B
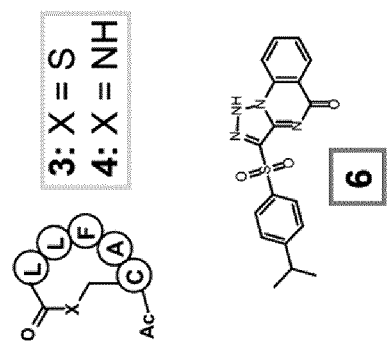
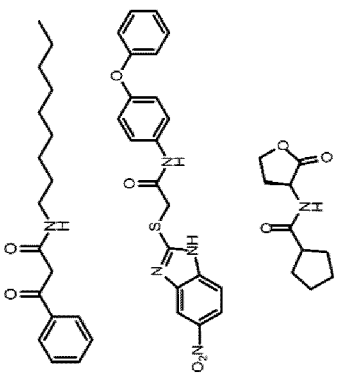
FIG. 6A
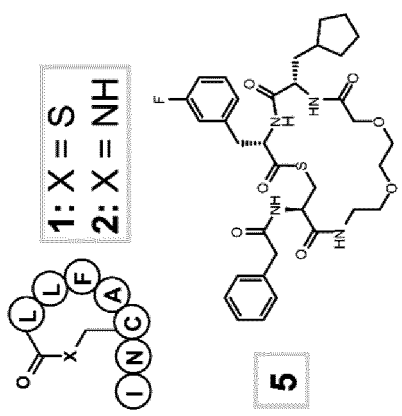
FIG. 6B

FIGS. 7A – 7D
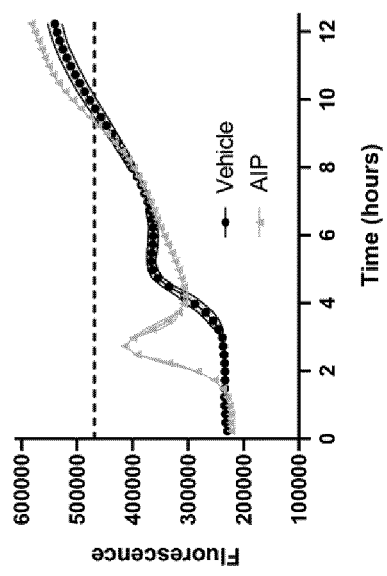
FIG. 7A
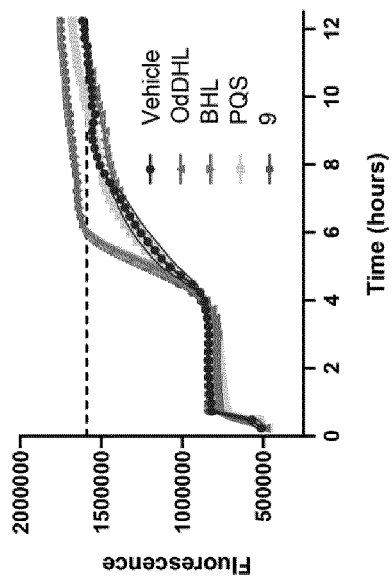
FIG. 7B
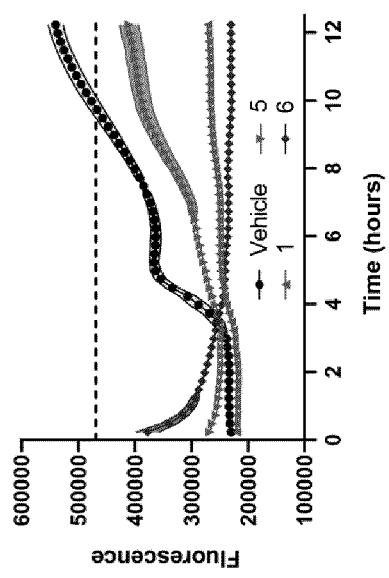
FIG. 7C
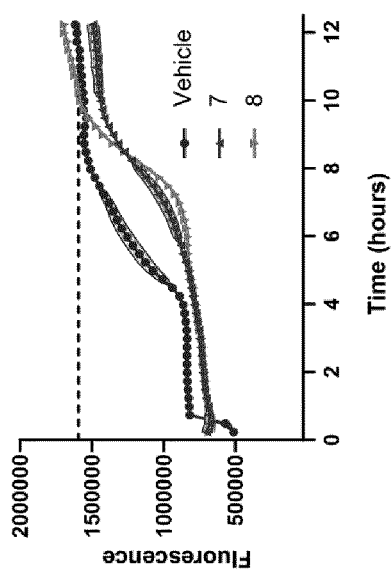
FIG. 7D

FIGS. 8A – 8C
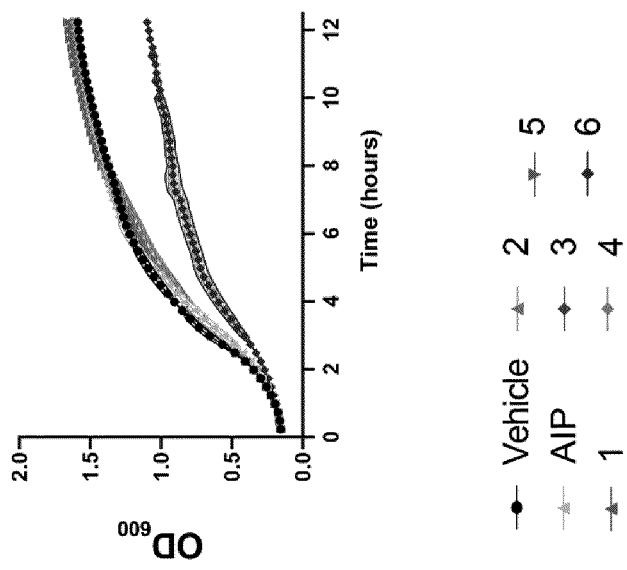
FIG. 8A
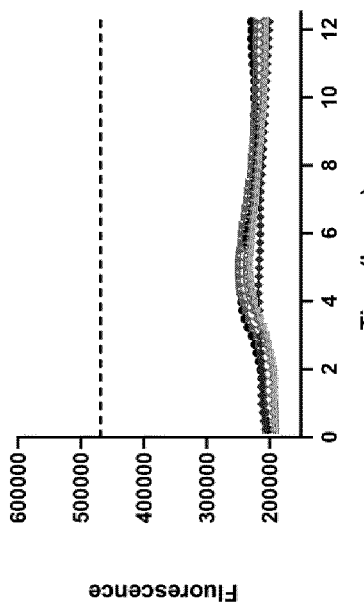
FIG. 8B
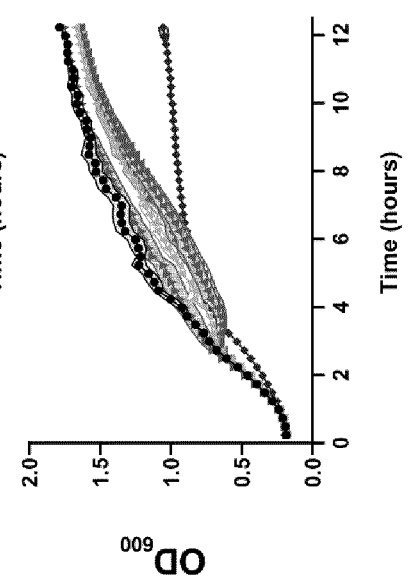
FIG. 8C

FIGS. 10A – 10C
FIG. 10A
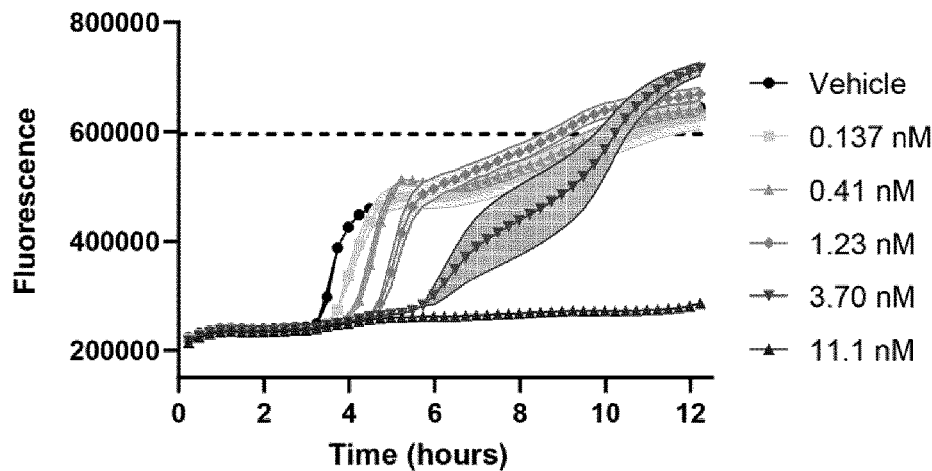
FIG. 10B
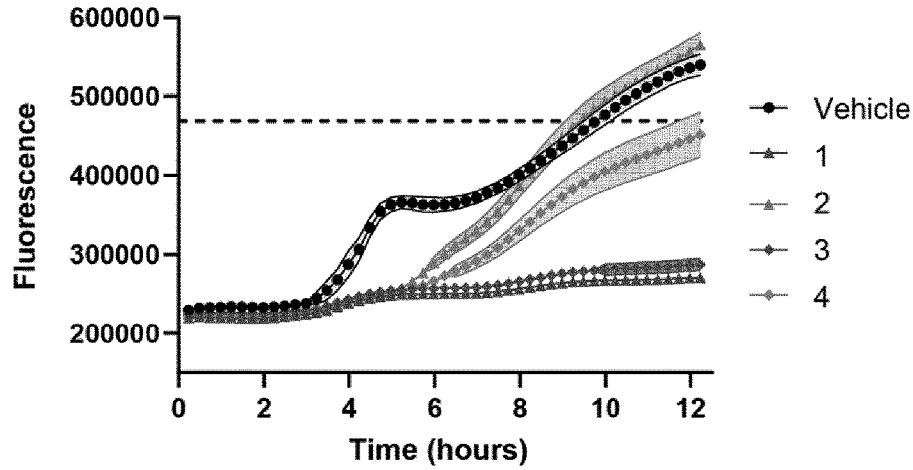
FIG. 10C
|   | IC$_{50}$ (nM) | Fluorescence (at 12 hr; a.u./10$^3$) |
|---|---|---|
| 1 | 0.485 | 270 |
| 2 | 1.20 | 560 |
| 3 | 0.257 | 290 |
| 4 | 1.50 | 450 |

FIGS. 11A – 11D
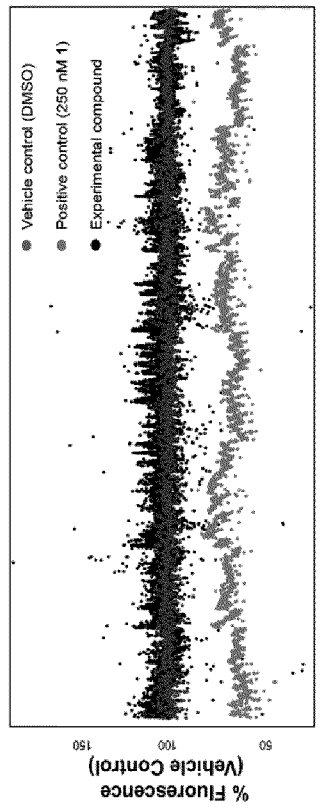
FIG. 11A
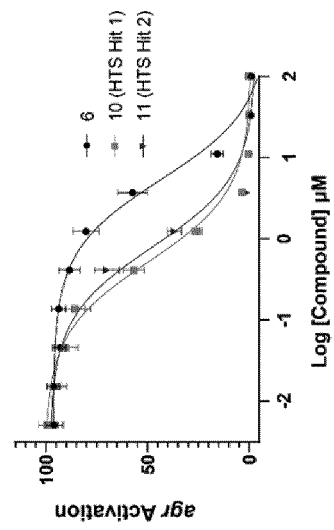
FIG. 11B
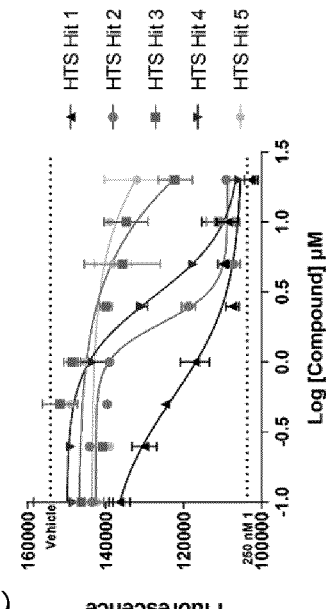
FIG. 11C
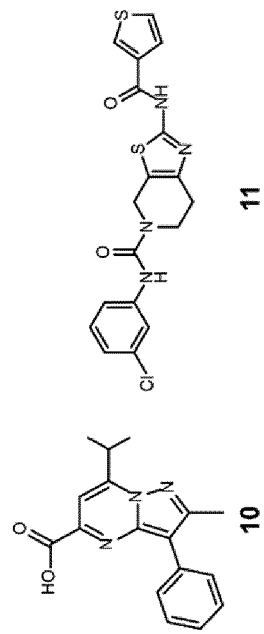
FIG. 11D

SYSTEM AND ASSAY FOR MONITORING PRODUCTION/RELEASE OF MEMBRANE-LYTIC TOXINS IN BACTERIA AND COMPOUNDS FOR MODULATING SAME

CROSS-REFERENCE TO RELATED APPLICATION

This application claims the benefit of and priority to U.S. patent application Ser. No. 63/237986, filed on Aug. 27, 2021, the contents of which are incorporated herein by reference in its entirety.

STATEMENT OF GOVERNMENT SUPPORT

This invention was made with government support under GM131817 and AI135745 awarded by the National Institutes of Health and under DMR1720415 awarded by the National Science Foundation. The government has certain rights in the invention.

FIELD

The present technology generally relates to systems and assays for monitoring production and/or release of membrane-lytic toxins (e.g., biosurfactants) in bacteria, optionally in the presence of a test compound. The present technology also relates to compounds and compositions for modulating, including inhibiting and activating, membrane-lytic toxin production/release and, in certain instances, quorum sensing in bacteria.

BACKGROUND

Bacteria can sense their population densities using low molecular weight signals and alter their behaviors at high cell numbers to act as a group. This cell-to-cell signaling process is called quorum sensing (QS) and its outcomes often have devastating impacts on human and animal health, agriculture, and a range of clinical and industrial environments. Staphylococcus aureus and Pseudomonas aeruginosa are two notorious pathogens that use QS to regulate toxin production/release and other behaviors that incur tremendous burdens on human health. S. aureus is a Gram-positive bacterium and, once achieving a sufficiently high (i.e., quorate) population, uses the accessory gene regulator (agr) QS system to produce protein-based toxins and a suite of peptides, called phenol-soluble modulins (PSMs), that exhibit membrane lytic activity. P. aeruginosa is a Gram-negative bacterium and uses a set of QS systems (i.e., LuxI/LuxR-type and Pqs) at high cell density to produce an analogous array of protein-based and small-molecule toxins, along with biosurfactants (i.e., rhamnolipids) that can disrupt lipid membranes and kill cells.

To date, the scope of compounds available as chemical modulators of QS (QSMs) in P. aeruginosa and S. aureus is limited. Several factors have complicated the discovery and characterization of new synthetic QSMs with improved properties. One factor is the assumption that new compounds identified to target a specific QS system or receptor in conventional cell-based assays using QS reporter gene constructs will ultimately translate directly to QS-linked phenotypes. This assumption is not always true in S. aureus and P. aeruginosa, however, because additional, and often indirect, pathways can also contribute to the control of virulence phenotypes. Conversely, assays based on phenotypic response (e.g., production of toxins, formation of biofilm, motility, etc.) are typically low-throughput and highly environmentally sensitive and, thus, not as well suited for discovery oriented research. Furthermore, the activity of QSMs in many model laboratory strains used to create QS transcriptional reporter systems for screening campaigns may not be representative of their activities in wild-type isolates. Indeed, a growing number of reports describing the functional role of S. aureus and P. aeruginosa QS networks in wild-type strains suggests that they can differ substantially from those of common laboratory strains.

SUMMARY OF THE PRESENT TECHNOLOGY

The present technology provides a system and assay for monitoring production/release of membrane-lytic toxins (e.g., phenol-soluble modulins, and biosurfactants such as rhamnolipids) by both Gram-positive and Gram-negative bacteria. As production of such toxins is controlled by quorum sensing mechanisms in some bacteria, the system and assays provide a way to monitor quorum sensing in such bacteria. More broadly, the system and assay may be used to assess bacterial production and/or release of membrane-lytic toxin by any mechanism. The system and assay may also be used to assess modulation of membrane-lytic toxin production/release, by a test compound. The system and assay thus allow for facile in situ screening of exogenous compounds capable of altering membrane-lytic toxin production/release by bacteria, and thereby identify new compounds that can modulate quorum sensing, while avoiding the constraints of many of the cell-based reporter assays and phenotypic assays commonly used up to now.

In one aspect, the present technology provides a system for monitoring production/release of membrane-lytic toxins by bacteria. The system includes bacteria that release at least one membrane-lytic toxin; synthetic lipid vesicles comprising an environmentally sensitive indicator, wherein the synthetic lipid vesicles release the environmentally sensitive indicator in the presence of an effective amount of the membrane-lytic toxins; and a growth medium; wherein the bacteria and synthetic lipid vesicles are in contact with the growth medium. In any embodiments, the bacteria release the at least one-membrane-lytic toxin when the bacteria are at a quorum-sensing density. In such embodiments, the system may be used for monitoring quorum sensing, including, optionally, in the presence of a test compound. In any embodiments, the synthetic lipid vesicles are not cross-linked. In any embodiments the environmentally sensitive indicator is an environmentally sensitive dye or particles.

In another aspect, the present technology provides compounds that may modulate production/release of membrane-lytic toxins and/or inhibit or activate quorum sensing in certain types of bacteria. Thus, the present technology provides compounds of Formula I or Formula II:

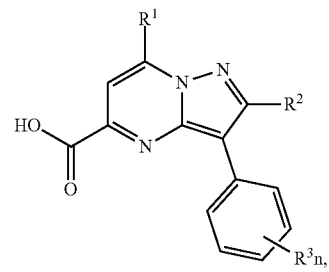

-continued

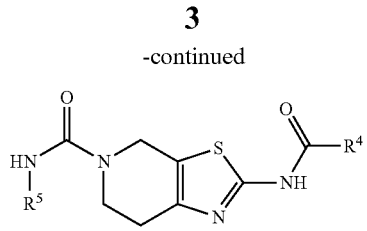

and/or a tautomer thereof and/or a pharmaceutically acceptable salt thereof,
wherein
$R^1$ is OH (or its oxo tautomer), or a substituted or unsubstituted alkyl, cycloalkyl, or cycloalkylalkyl group;
$R^2$ is H, halogen, OH, $NO_2$, or a substituted or unsubstituted alkyl, cycloalkyl or cycloalkylalkyl group;
$R^3$ is a halogen, CN, $NO_2$, or a substituted or unsubstituted alkyl, cycloalkyl, or cycloalkylalkyl group; and
$R^4$ is $OR^a$, $NHR^a$, or a substituted or unsubstituted alkyl, cycloalkyl, cycloalkylalkyl, aryl, aralkyl, heteroaryl, or heteroarylalkyl group;
$R^5$ is a substituted or unsubstituted alkyl, cycloalkyl, cycloalkylalkyl, aryl, aralkyl, heteroaryl, or heteroarylalkyl group;
$R^a$ is substituted or unsubstituted alkyl, cycloalkyl, cycloalkylalkyl, aryl, aralkyl, heteroaryl, or heteroarylalkyl group; and
n is 1, 2, 3, 4 or 5;
provided that the compound is not 7-isopropyl-2-methyl-3-phenylpyrazolo[1,5-a]pyrimidine-5-carboxylic acid, and is not N-(3-chlorophenyl)-2-(thiophene-3-carboxamido)-6,7-dihydrothiazolo[5,4-c]pyridine-5(4H)-carboxamide.

In another aspect, the present technology provides a pharmaceutical composition comprising a compound of Formula I or Formula II as described herein and a pharmaceutically acceptable carrier and/or excipient.

In another aspect, the present technology provides methods of modulating production/release of a membrane-lytic toxin by bacteria comprising contacting the bacteria with an effective amount of any compound as described herein (e.g., a compound of Formula I or II). In any embodiments, the bacteria release the membrane-lytic toxin upon reaching a quorum-sensing density. Thus, the compound may activate QS or may inhibit QS. In any embodiments, the compound is QS inhibitor.

In another aspect, the present technology provides methods for treating a bacterial infection in a subject comprising administering an effective amount of a compound described herein (e.g., a QS inhibitor) to the subject.

BRIEF DESCRIPTION OF THE DRAWINGS

FIGS. 1A-1C show how S. aureus and P. aeruginosa regulate virulence factor (e.g., membrane-lytic toxin) production through QS signaling. (1A) Schematic of the S. aureus accessory gene regulator (agr) system. S. aureus uses QS to upregulate myriad toxins, including phenol soluble modulins (PSMs). (1B) Schematic of the Las-Rhl-Pqs P. aeruginosa QS system. Rhamnolipid production by P. aeruginosa is induced by activation of the LuxI/LuxR-type Rhl QS system. Another LuxI/LuxR-type circuit, Las, is responsible for activation of Rhl, in coordination with the Pseudomonas quinolone signaling (PQS) system. (1C) The structures of the native QS signaling molecules and relevant amphiphilic toxins of both species, including the hemolytic S. aureus δ-toxin (one of several PSM types). Colored boxes around compound names indicate cellular targets in panels 1A and 1B. AIP and δ-toxin structures are shown with single-letter amino acid codes. Yellow and red shading in δ-toxin indicate hydrophobic and hydrophilic residues, respectively; the two views highlight its overall amphipathic structure. Structure for δ-toxin retrieved from the Protein Data Bank; PDB ID=2KAM (Loureiro-Ferreira, 2008).

FIGS. 2A-2D show vesicle lysis occurring in the presence of bacteria for an illustrative embodiment of present technology. (2A-B) Differential vesicle lysis between WT (black) and QS mutant (grey) strains of S. aureus (A) and P. aeruginosa (2B) as measured by fluorescence over time. (2C-D) Vesicle lysis (black) induced by WT S. aureus (2C) and P. aeruginosa (2D) correlated with QS-onset as determined by transcriptional reporter strains ((green) S. aureus containing agr reporter plasmid pDB59, producing YFP; P. aeruginosa containing plasI-LVAgfp reporter plasmid, producing GFP; see General Methods and Table 1 for details). The dashed line in (2A, 2B) indicates fluorescence one hr after addition of the positive lysis control (Triton X-100). Data points represent the mean of all replicates (n=9). Error bars=SEM (shaded area around data points).

FIGS. 3A-3C show results of dynamic light scattering (DLS) analysis of the calcein-loaded vesicle formulations of an illustrative embodiment disclosed in the Examples. Intensity and number average size distributions for vesicles composed of (A) 68% DPPC, 30% cholesterol, and 2% DPPE and (3B, 3C) 70% DOPC and 30% cholesterol passed through a 100 nm polycarbonate membrane either (3B) 3 times (representative of vesicles used in high-throughput assays) or (3A, 3C) 7 times (representative of vesicles used in continuous time course experiments). These DLS results demonstrate that the vesicles used in this work are ~150 nm in diameter. Size distributions shown are the average of three independent measurements of a single vesicle sample.

FIGS. 4A-4D show growth curves for bacteria incubated in the presence of calcein-loaded vesicles of an illustrative embodiment disclosed in the Examples. (4A) Growth curves for S. aureus WT and an agr-null strain (S. aureus QS mutant). (4B) Growth curves for P. aeruginosa WT and a ΔlasRrhlR strain (P. aeruginosa QS mutant). (4C) Growth curves for S. aureus WT with vesicles and S. aureus WT containing a YFP QS reporter plasmid (pDB59). (4D) Growth curves for P. aeruginosa WT with vesicles and P. aeruginosa WT containing a GFP QS reporter plasmid (plasI-LVAgfp). Data points represent the mean of all replicates (n=9). Error bars=SEM (shaded area around data points). See General Methods for assay protocols and Table 1 for details of strains and plasmids used.

FIGS. 5A-5B show normalized calcein fluorescence intensity values for (5A) rhamnolipid introduced to 68% DPPC, 30% cholesterol, 2% DPPE vesicles containing calcein in calcein buffer (the vesicles used for experiments with P. aeruginosa) at various concentrations and (5B) PSMα3 introduced to 70% DOPC, 30% cholesterol vesicles containing calcein in PBS (the vesicles used for experiments with S. aureus) at various concentrations. In all measurements, the lipid concentration of the vesicles was held constant at 100 μM for P. aeruginosa vesicles or 200 μM for S. aureus vesicles. All points shown are the mean and SD of three measurements of a single technical replicate. In both plots, some error bars are obscured by the sizes of the data points. See Methods for details of each vesicle formulation.

FIGS. 6A-6B show non-native QSMs of S. aureus (6A) and P. aeruginosa (6B) evaluated in the Examples: Synthetic S. aureus QS antagonists (1-6), P. aeruginosa QS antagonists (7, 8), and synthetic QS agonist (9). Common compound names: 1, AIP III D4A; 2, AIP III D4A amide; 3, tr. AIP III D2A; 4, tr. AIP III D2A amide; 5, Bnc3; 6, savirin; 7, V-06-018; 8, M64. tr.=truncated. Colored boxes indicate the cellular targets color-coded in FIGS. 1A-1B: green=AgrC; red=AgrA; purple=LasR; blue=RhlR; orange=PqsR.

FIGS. 7A-7D show vesicle lysis is strongly influenced by exogenously added QSMs in an illustrative embodiment in the Examples. Fluorescence was monitored for 12 hr after incubation of lag phase WT bacteria with vesicle suspensions and QSMs. (7A) QS inhibitors 1, 5, and 6 repress vesicle lysis in *S. aureus*, whereas (7B) the native ALP induces early lysis. (7C) QS inhibitors 7 and 8 delay the onset of vesicle lysis by approximately 2 hr in *P. aeruginosa*. (7D) RhlR activators BHL and 9 facilitate vesicle lysis in *P. aeruginosa*, while the native agonists of LasR and RhlR, OdDHL and PQS, had no observable effect. The dashed line indicates fluorescence 1 hr after addition of the positive lysis control (Triton X-100). Vehicle=DMSO. Data points represent the mean of all replicates (n=9). Error bars=SEM (shaded area around data points).

FIGS. 8A-8C show the effects of exogenously added AIP and compounds 1-6 on vesicle lysis and *S. aureus* growth. Compounds and corresponding colors/symbols are shown at lower right. (8A) Fluorescence curves for vesicles incubated with the *S. aureus* QS mutant+vehicle and/or compounds. The dashed line indicates fluorescence 1 hr after addition of Triton X-100 (positive control for complete vesicle lysis). Compounds did not have a noticeable effect on vesicle lysis. (8B) Growth curves for *S. aureus* WT incubated with vesicles+vehicle/compounds. (8C) Growth curves for the *S. aureus* QS mutant incubated with vesicles+vehicle/compounds. Data points represent the mean of all replicates (n=9). Error bars=SEM (shaded area around data points). See Methods for full details of assays.

FIGS. 10A-10C show the timing and magnitude of vesicle lysis is dependent on QSM concentration and potency. (10A) Fluorescence as measured over time for a *S. aureus*-vesicle mixture treated with QS antagonist 1 at varying concentrations. (10B) Fluorescence as measured over time for a *S. aureus*-vesicle mixture treated with QS inhibitors 1-4 at 100 nM; 1-4 are structurally related compounds with similar, yet distinct, $IC_{50}$ values in cell-based reporter assays. The dashed lines indicate fluorescence one hr after addition of the positive lysis control (Triton X-100). Vehicle=DMSO. Data points represent the mean of all replicates (n=9). Error bars=SEM (shaded area around data points). (10C) $IC_{50}$ values for 1-4 in cell-based reporter assays (reproduced from (Tal-Gan et al., 2016)) correlate with vesicle leakage as measured by fluorescence after 12 hr (a.u.=arbitrary units).

FIGS. 11A-11D provide a summary of high-throughput screening results. (11A) A scatter plot was generated for the primary screen of test compounds. Test compounds (black) that resulted in less than 80% fluorescence relative to vehicle controls (blue) were selected for secondary screening to confirm activity. Positive controls (red) typically yielded fluorescence values between 50% and 70% of the vehicle controls. (11B) Dose-response analysis of select high-throughput screening (HTS) hit compounds using the vesicle leakage assay. Of the 14 compounds selected for dose-response analysis, five indicated probable inhibition of biosurfactant production and were subjected to further analysis using an agr YFP transcriptional reporter. Error bars indicate SD. Vehicle and positive controls (dashed lines) are also shown. (11C) Dose-response analysis for high-throughput screen (HTS) hit compounds 1 and 2 using an agr YFP transcriptional reporter. Error bars indicate SEM. (11D) Structure of novel agr inhibitors 10 and 11 identified using this high-throughput screen.

DETAILED DESCRIPTION

Figures 9A, 9B, 9C:
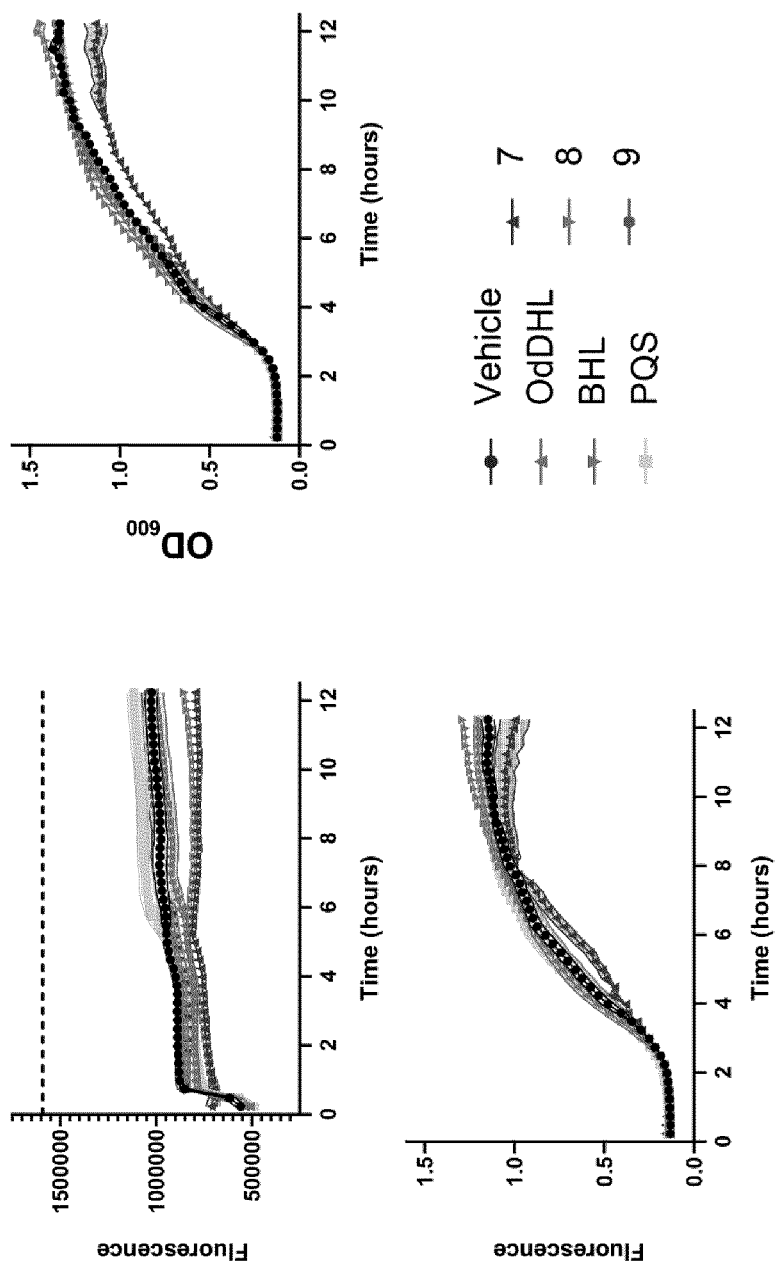
FIGS. 9A-9C show effects of exogenously added native QS signaling molecules (OdDHL, BHL, and PQS) and compounds 7-9 on vesicle lysis and *P. aeruginosa* growth. Compounds and corresponding colors/symbols are shown at lower right. (9A) Fluorescence curves for vesicles incubated with the *P. aeruginosa* QS mutant+vehicle and/or compounds. The dashed line indicates fluorescence 1 hr after addition of Triton X-100 (positive control for complete vesicle lysis). Compounds did not have a noticeable effect on vesicle lysis. (9B) Growth curves for WT *P. aeruginosa* incubated with vesicles+vehicle/compounds. (9C) Growth curves for the *P. aeruginosa* QS mutant incubated with vesicles+vehicle/compounds. Data points represent the mean of all replicates (n=9). Error bars=SEM (shaded area around data points). See Methods for full details of assays.

The following terms are used throughout as defined below. All other terms and phrases used herein have their ordinary meanings as one of skill in the art would understand.

As used herein and in the appended claims, singular articles such as "a" and "an" and "the" and similar referents in the context of describing the elements (especially in the context of the following claims) are to be construed to cover both the singular and the plural, unless otherwise indicated herein or clearly contradicted by context. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the embodiments and does not pose a limitation on the scope of the claims unless otherwise stated. No language in the specification should be construed as indicating any non-claimed element as essential.

As used herein, "about" will be understood by persons of ordinary skill in the art and will vary to some extent depending upon the context in which it is used. If there are uses of the term that are not clear to persons of ordinary skill in the art, given the context in which it is used, "about" will mean up to plus or minus 10% of the particular term unless otherwise stated or otherwise evident from the context (e.g., where such number would be less than 0% or exceed 100% of a possible value).

"Effective amount" refers to the amount of compound or composition required to produce a desired effect. As the compounds of the present technology may be used in different contexts, the effective amounts may vary with the context in which the compounds are used. For example, an effective amount of membrane-lytic toxins may be an amount that causes release of an environmentally sensitive dye from synthetic lipid vesicles. In another example, an effective amount of a compound or composition may be one that inhibits production and/or release of a membrane-lytic toxin and/or inhibits quorum sensing in bacteria. An effective amount in such contexts may include amounts that slow, reduce, eliminate or otherwise inhibit the ability of bacteria to release membrane-lytic toxins and/or other toxins including, e.g., when the bacteria reach a quorate population and would otherwise produce and release such factors and toxins. In the context of treatment of a subject, the "effective amount" (i.e., "a therapeutically effective amount") refers to an amount of the compound or composition that alleviates, in whole or in part, symptoms associated with a disorder or disease (e.g., bacterial infection), or slows or halts further progression or worsening of those symptoms/outcomes, e.g., by inhibiting release of a membrane-lytic toxin and/or quorum sensing. In the context of prevention, an effective amount prevents or provides prophylaxis at least in part for the disease or disorder in a subject at risk for developing the disease or disorder. One example of an effective amount includes amounts or dosages that yield acceptable toxicity and bioavailability levels for therapeutic (pharmaceutical) use. Determining an effective amount of a compound described herein for reducing bacterial virulence, inhibiting production and/or release of membrane-lytic toxins (e.g., biosurfactants) or treating a bacterial infection is well within the skill in the art in view of the present disclosure. Similarly, determining effective amounts of a compound herein for modulating quorum sensing (including activating or inhibiting) is within the skill in the art in view of the guidance provided herein and the general knowledge in the field.

As used herein, a "subject" or "patient" is any animal subject to bacterial infections. In any embodiments, the subject is a human or non-human animal, such as a cat, dog, bird, fish, ungulate, rodent or primate. In any embodiments, the subject is a human. The term "subject" and "patient" can be used interchangeably.

"Treating" or "treatment" within the context of the present technology, means an alleviation, in whole or in part, of symptoms associated with a disorder or disease, or slowing, or halting of further progression or worsening of those symptoms. As a non-limiting example of treatment, a subject can be successfully treated for a bacterial infection if, after receiving through administration an effective or therapeutically effective amount of one or more compounds or compositions described herein, the subject shows observable and/or measurable improvements such as reduction or elimination of bacterial load, fever, muscle aches, headache, nausea, vomiting, stiff neck, confusion, loss of balance, convulsions. Treatment, as defined herein, may include administering a compound herein to prevent infection, that is, administering the compound beforehand to avert or forestall the appearance of one or more symptoms of a disease or disorder, such as bacterial infection. It will be appreciated by one of skill in the art that prevention is not used as an absolute term. in the medical art it is understood to refer to the prophylactic administration of a drug to substantially diminish the likelihood or seriousness of a condition, or symptom of the condition and this is the sense intended in this disclosure. As used in a standard text in the field, the Physician's Desk Reference, the terms "prevent", "preventing" and "prevention" with regard to a disorder or disease, refer to averting the cause, effects, symptoms or progression of a disease or disorder prior to the disease or disorder fully manifesting itself Treatment typically refers to the administration of an effective amount of a compound of the present technology to a subject.

Pharmaceutically acceptable salts of compounds described herein are within the scope of the present technology and include acid or base addition salts which retain the desired pharmacological activity and are not biologically undesirable (e.g., the salt is not unduly toxic, allergenic, or irritating, and is bioavailable). When the compound of the present technology has a basic group, such as, for example, an amino group, pharmaceutically acceptable salts can be formed with inorganic acids (such as hydrochloric acid, hydrobromic acid, nitric acid, sulfuric acid, and phosphoric acid), organic acids (e.g., alginate, formic acid, acetic acid, benzoic acid, gluconic acid, fumaric acid, oxalic acid, tartaric acid, lactic acid, maleic acid, citric acid, succinic acid, malic acid, methanesulfonic acid, benzenesulfonic acid, naphthalene sulfonic acid, and p-toluenesulfonic acid) or acidic amino acids (such as aspartic acid and glutamic acid). When the compound of the present technology has an acidic group, such as for example, a carboxylic acid group, it can form salts with metals, such as alkali and earth alkali metals (e.g., $Na^+$, $Li^+$, $K^+$, $Ca^{2+}$, $Mg^{2+}$, $Zn^{2+}$), ammonia or organic amines (e.g., dicyclohexylamine, trimethylamine, triethylamine, pyridine, picoline, ethanolamine, diethanolamine, triethanolamine) or basic amino acids (e.g., arginine, lysine and ornithine). Such salts can be prepared in situ during isolation and purification of the compounds or by separately reacting the purified compound in its free base or free acid form with a suitable acid or base, respectively, and isolating the salt thus formed.

As used herein, the term "membrane-lytic toxin" refers to an agent released by bacteria which can lyse or cause lysis of host cell membranes. Membrane-lytic toxins vary by bacterial species and include amphipathic peptides known as phenol-soluble modulins (PSMs) produced by *S. aureus* and rhamnolipids produced by *P. aeruginosa*.

As used herein, the term "quorum-sensing density" refers to the cell population density at which a species or strain of bacteria produces and releases membrane-lytic toxins. The quorum-sensing density may vary by bacterial species, strain and environmental conditions, and is often in the range of $10^7$-$10^9$ cells/mL.

Those of skill in the art will appreciate that compounds of the present technology may exhibit the phenomena of tautomerism, conformational isomerism, geometric isomerism and/or stereoisomerism. As the formula drawings within the specification and claims can represent only one of the possible tautomeric, conformational isomeric, stereochemical or geometric isomeric forms, it should be understood that the present technology encompasses any tautomeric, conformational isomeric, stereochemical and/or geometric isomeric forms of the compounds having one or more of the utilities described herein, as well as mixtures of these various different forms.

"Tautomers" refers to isomeric forms of a compound in equilibrium with each other, wherein the isomers differ by the position of a hydrogen atom. Common examples of tautomers include keto-enol tautomers and guanidine tautomers. The presence and concentrations of the isomeric forms will depend on the environment the compound is found in and may be different depending upon, for example, whether the compound is a solid or is in an organic or aqueous solution. Because of the limits of representing compounds by structural formulas, it is to be understood that all chemical formulas of the compounds described herein represent all tautomeric forms of compounds and are within the scope of the present technology.

Stereoisomers of compounds (also known as optical isomers) include all chiral, diastereomeric, and racemic forms of a structure, unless the specific stereochemistry is expressly indicated. Thus, compounds used in the present technology include enriched or resolved optical isomers at any or all asymmetric atoms as are apparent from the depictions. Both racemic and diastereomeric mixtures, as well as the individual optical isomers can be isolated or synthesized so as to be substantially free of their enantiomeric or diastereomeric partners, and these stereoisomers are all within the scope of the present technology.

The compounds of the present technology may exist as solvates, especially hydrates. Hydrates may form during manufacture of the compounds or pharmaceutical compositions comprising the compounds, or hydrates may form over time due to the hygroscopic nature of the compounds. Compounds of the present technology may exist as organic solvates as well, including DMF, ether, and alcohol solvates among others. The identification and preparation of any particular solvate is within the skill of the ordinary artisan of synthetic organic or medicinal chemistry.

Generally, reference to a certain element such as hydrogen or H is meant to include all isotopes of that element. For example, if an R group is defined to include hydrogen or H, it also includes deuterium and tritium. Compounds comprising radioisotopes such as tritium, $C^{14}$, $P^{32}$ and $S^{35}$ are thus within the scope of the present technology. Procedures for inserting such labels into the compounds of the present technology will be readily apparent to those skilled in the art based on the disclosure herein.

In general, "substituted" refers to an organic group as defined below (e.g., an alkyl group) in which one or more bonds to a hydrogen atom contained therein are replaced by a bond to a non-hydrogen atom. Substituted groups also include groups in which one or more bonds to a carbon(s) or hydrogen(s) atom are replaced by one or more bonds, including double or triple bonds, to a heteroatom. Thus, a substituted group is substituted with one or more substituents, unless otherwise specified. In some embodiments, a substituted group is substituted with 1, 2, 3, 4, 5, or 6 substituents. Examples of substituent groups include, but are not limited to, alkyl, alkenyl, halogen (i.e., F, Cl, Br, and I); hydroxyl; hydroxyalkyl, alkoxy, alkenoxy, aryloxy, aralkyloxy, heterocyclyl, heterocyclylalkyl, heterocyclyloxy, and heterocyclylalkoxy groups; carbonyl (oxo); carboxylate; ester; urethane; oximes; hydroxylamine; alkoxyamine; aralkoxyamine; thiol; alkylthio; sulfide; sulfoxide; sulfone; sulfonyl; sulfonamide; amine; N-oxide; hydrazine; hydrazide; hydrazone; azide; amide; urea; amidine; guanidine; enamine; imide; isocyanate; isothiocyanate; cyanate; thiocyanate; imine; nitro; nitrile (i.e., CN); and the like.

As to any of the groups herein which contain one or more substituents, it is understood, that such groups do not contain any substitution or substitution patterns that are sterically impractical and/or synthetically non-feasible. In addition, the compounds of this invention include all stereochemical isomers arising from the substitution of these compounds.

As used herein, $C_m-C_n$, such as $C_1-C_{12}$, $C_1-C_6$, or $C_1-C_3$ when used before a group refers to that group containing m to n carbon atoms.

Alkyl groups include straight chain and branched chain alkyl groups having from 1 to 12 carbon atoms, and typically from 1 to 10 carbons or, in some embodiments, from 1 to 8, 1 to 6, or 1 to 3 carbon atoms. Examples of straight chain alkyl groups include, but are not limited to, groups such as methyl, ethyl, n-propyl, n-butyl, n-pentyl, n-hexyl, n-heptyl, and n-octyl groups. Examples of branched alkyl groups include, but are not limited to, isopropyl, iso-butyl, sec-butyl, tent-butyl, neopentyl, isopentyl, and 2,2-dimethylpropyl groups. Alkyl groups may be substituted or unsubstituted. Representative substituted alkyl groups may be substituted one or more times with substituents such as those listed above, and include without limitation haloalkyl (e.g., trifluoromethyl), hydroxyalkyl, thioalkyl, aminoalkyl, alkylaminoalkyl, dialkylaminoalkyl, alkoxyalkyl, carboxyalkyl, and the like.

Specific substituted alkyl groups include haloalkyl groups, particularly trihalomethyl groups and specifically trifluoromethyl groups. Specific substituted aryl groups include mono-, di-, tri, tetra- and pentahalo-substituted phenyl groups; mono-, di-, tri-, tetra-, penta-, hexa-, and hepta-halo-substituted naphthalene groups; 3- or 4-halo-substituted phenyl groups, 3- or 4-alkyl-substituted phenyl groups, 3- or 4-alkoxy-substituted phenyl groups, 3- or 4-RCO-substituted phenyl, 5- or 6-halo-substituted naphthalene groups. More specifically, substituted aryl groups include acetylphenyl groups, particularly 4-acetylphenyl groups; fluorophenyl groups, particularly 3-fluorophenyl and 4-fluorophenyl groups; chlorophenyl groups, particularly 3-chlorophenyl and 4-chlorophenyl groups; methylphenyl groups, particularly 4-methylphenyl groups, and methoxyphenyl groups, particularly 4-methoxyphenyl groups.

Alkenyl groups include straight and branched chain alkyl groups as defined above, except that at least one double bond exists between two carbon atoms. Alkenyl groups have from 2 to 12 carbon atoms, and typically from 2 to 10 carbons or, in some embodiments, from 2 to 8, 2 to 6, or 2 to 4 carbon atoms. In some embodiments, the alkenyl group has one, two, or three carbon-carbon double bonds. Examples include, but are not limited to vinyl, allyl, —CH═CH(CH₃), —CH═C(CH₃)₂, —C(CH₃)═CH₂, —C(CH₃)═CH(CH₃), —C(CH₂CH₃)═CH₂, among others. Representative substituted alkenyl groups may be mono-substituted or substituted more than once, such as, but not limited to, mono-, di- or tri-substituted with substituents such as those listed above.

Alkoxy groups are hydroxyl groups (-OH) in which the bond to the hydrogen atom is replaced by a bond to a carbon atom of a substituted or unsubstituted alkyl group as defined above. Examples of linear alkoxy groups include, but are not limited to, methoxy, ethoxy, propoxy, butoxy, pentoxy, hexoxy, and the like. Examples of branched alkoxy groups include, but are not limited to, isopropoxy, sec-butoxy, tent-butoxy, isopentoxy, isohexoxy, and the like. Examples of cycloalkoxy groups include, but are not limited to, cyclopropyloxy, cyclobutyloxy, cyclopentyloxy, cyclohexyloxy, and the like. Alkoxy groups may be substituted or unsubstituted. Representative substituted alkoxy groups may be substituted one or more times with substituents such as those listed above.

Alkynyl groups include straight and branched chain alkyl groups as defined above, except that at least one triple bond exists between two carbon atoms. Alkynyl groups have from 2 to 12 carbon atoms, and typically from 2 to 10 carbons or, in some embodiments, from 2 to 8, 2 to 6, or 2 to 4 carbon atoms. In some embodiments, the alkynyl group has one, two, or three carbon-carbon triple bonds. Examples include, but are not limited to —C≡CH, —C≡CCH₃, —CH₂C≡CCH₃, —C≡CCH₂CH(CH₂CH₃)₂, among others. Representative substituted alkynyl groups may be mono-substituted or substituted more than once, such as, but not limited to, mono-, di- or tri-substituted with substituents such as those listed above.

Aryl groups are cyclic aromatic hydrocarbons that do not contain heteroatoms. Aryl groups herein include monocyclic, bicyclic and tricyclic ring systems. Thus, aryl groups include, but are not limited to, phenyl, azulenyl, heptalenyl, biphenyl, fluorenyl, phenanthrenyl, anthracenyl, indenyl, indanyl, pentalenyl, and naphthyl groups. In some embodiments, aryl groups contain 6-14 carbons, and in others from 6 to 12 or even 6-10 carbon atoms in the ring portions of the groups. In some embodiments, the aryl groups are phenyl or naphthyl. Although the phrase "aryl groups" includes groups containing fused rings, such as fused aromatic-aliphatic ring systems (e.g., indanyl, tetrahydronaphthyl, and the like), it does not include aryl groups that have other groups, such as alkyl or halo groups, bonded to one of the ring members. Rather, groups such as tolyl are referred to as substituted aryl groups. Aryl groups may be substituted or unsubstituted. Representative substituted aryl groups may be mono-substituted or substituted more than once. For example, mono-substituted aryl groups include, but are not limited to, 2-, 3-, 4-, 5-, or 6-substituted phenyl or naphthyl groups, which may be substituted with substituents such as those listed above.

Aralkyl groups are alkyl groups as defined above in which a hydrogen or carbon bond of an alkyl group is replaced with a bond to an aryl group as defined above. In some embodiments, aralkyl groups contain 7 to 16 carbon atoms, 7 to 14 carbon atoms, or 7 to 10 carbon atoms. Aralkyl groups may be substituted or unsubstituted. Substituted aralkyl groups may be substituted at the alkyl, the aryl or both the alkyl and aryl portions of the group. Representative aralkyl groups include but are not limited to benzyl and phenethyl groups and fused (cycloalkylaryl)alkyl groups such as 4-indanylethyl. Representative substituted aralkyl groups may be substituted one or more times with substituents such as those listed above.

Cycloalkyl groups include mono-, bi- or tricyclic alkyl groups having from 3 to 12 carbon atoms in the ring(s), or, in some embodiments, 3 to 10, 3 to 8, or 3 to 4, 5, or 6 carbon atoms. Exemplary monocyclic cycloalkyl groups include, but not limited to, cyclopropyl, cyclobutyl, cyclopentyl, cyclohexyl, cycloheptyl, and cyclooctyl groups. In some embodiments, the cycloalkyl group has 3 to 8 ring members, whereas in other embodiments the number of ring carbon atoms range from 3 to 5, 3 to 6, or 3 to 7. Bi- and tricyclic ring systems include both bridged cycloalkyl groups and fused rings, such as, but not limited to, bicyclo[2.1.1]hexane, adamantyl, decalinyl, and the like. Substituted cycloalkyl groups may be substituted one or more times with, non-hydrogen groups, including heteroatoms, as defined above. However, substituted cycloalkyl groups also include rings that are substituted with straight or branched chain alkyl or alkenyl groups as defined above. Representative substituted cycloalkyl groups may be mono-substituted or substituted more than once, such as, but not limited to, 2,2-, 2,3-, 2,4- 2,5- or 2,6-disubstituted cyclohexyl groups, which may be substituted with substituents such as those listed above.

Cycloalkylalkyl groups are alkyl groups as defined above in which a hydrogen or carbon bond of an alkyl group is replaced with a bond to a cycloalkyl group as defined above. In some embodiments, cycloalkylalkyl groups have from 4 to 16 carbon atoms, 4 to 12 carbon atoms, and typically 4 to 10 carbon atoms. Substituted cycloalkylalkyl groups may be substituted at the alkyl, the cycloalkyl or both the alkyl and cycloalkyl portions of the group. Representative substituted cycloalkylalkyl groups may be mono-substituted or substituted more than once, such as, but not limited to, mono-, di- or tri-substituted with sub stituents such as those listed above.

Heteroalkyl groups are $C_{2-12}$ alkyl groups as described above, in which 1, 2, 3, 4, 5, or 6 carbon atoms are replaced with N, O, S, or combinations thereof, in a stable configuration. Thus, the heteroalkyl groups may include for example, NH, O, S, S(O) and $SO_2$ groups. Heteroalkyl groups have at least one carbon and do not include groups bearing adjacent heteroatoms (e.g., peroxides). In any embodiments, heteroalkyl groups include one or two heteroatoms selected from NH, O and S, wherein each heteroatom may be the same or different. Where valence allows, heteroalkyl groups may be further substituted with substituents as described herein. Examples of heteroalkyl groups include, but are not limited —$CH_2CH_2SCH_3$, —$CH_2CH_2OCH_2CH_3$, —$CH_2CH_2N(CH_3)CH_2SCH_3$, —$OCH_2CH_2OCH_2CH_2OCH_3$, —$CH_2S(O)CH_2$, —$CH_2CH_2SO_2CH_3$, and the like, as well as, e.g., polyether and polyamino alkyl groups, including but not limited to poly(oxyalkylene) groups.

Heterocyclyl groups include aromatic (also referred to as heteroaryl) and non-aromatic ring compounds containing 3 or more ring members, of which one or more is a heteroatom such as, but not limited to, N, O, and S. In some embodiments, the heterocyclyl group contains 1, 2, 3 or 4 heteroatoms. In some embodiments, heterocyclyl groups include mono-, bi- and tricyclic rings having 3 to 16 ring members, whereas other such groups have 3 to 6, 3 to 10, 3 to 12, or 3 to 14 ring members. Heterocyclyl groups encompass aromatic, partially unsaturated and saturated ring systems, such as, for example, imidazolyl, imidazolinyl and imidazolidinyl groups. The phrase "heterocyclyl group" includes fused ring species including those comprising fused aromatic and non-aromatic groups, such as, for example, benzotriazolyl, 2,3-dihydrobenzo[1,4]dioxinyl, and benzo[1,3]dioxolyl. The phrase also includes bridged polycyclic ring systems containing a heteroatom such as, but not limited to, quinuclidyl. However, the phrase does not include heterocyclyl groups that have other groups, such as alkyl, oxo or halo groups, bonded to one of the ring members. Rather, these are referred to as "substituted heterocyclyl groups". Heterocyclyl groups include, but are not limited to, aziridinyl, azetidinyl, pyrrolidinyl, imidazolidinyl, pyrazolidinyl, thiazolidinyl, tetrahydrothiophenyl, tetrahydrofuranyl, dioxolyl, furanyl, thiophenyl, pyrrolyl, pyrrolinyl, imidazolyl, imidazolinyl, pyrazolyl, pyrazolinyl, triazolyl, tetrazolyl, oxazolyl, isoxazolyl, thiazolyl, thiazolinyl, isothiazolyl, thiadiazolyl, oxadiazolyl, piperidyl, piperazinyl, morpholinyl, thiomorpholinyl, tetrahydropyranyl, tetrahydrothiopyranyl, oxathiane, dioxyl, dithianyl, pyranyl, pyridyl, pyrimidinyl, pyridazinyl, pyrazinyl, triazinyl, dihydropyridyl, dihydrodithiinyl, dihydrodithionyl, homopiperazinyl, quinuclidyl, indolyl, indolinyl, isoindolyl, azaindolyl (pyrrolopyridyl), indazolyl, indolizinyl, benzotriazolyl, benzimidazolyl, benzofuranyl, benzothiophenyl, benzthiazolyl, benzoxadiazolyl, benzoxazinyl, benzodithiinyl, benzoxathiinyl, benzothiazinyl, benzoxazolyl, benzothiazolyl, benzothiadiazolyl, benzo[1,3]dioxolyl, pyrazolopyridyl, imidazopyridyl (azabenzimidazolyl), triazolopyridyl, isoxazolopyridyl, purinyl, xanthinyl, adeninyl, guaninyl, quinolinyl, isoquinolinyl, quinolizinyl, quinoxalinyl, quinazolinyl, cinnolinyl, phthalazinyl, naphthyridinyl, pteridinyl, thianaphthyl, dihydrobenzothiazinyl, dihydrobenzofuranyl, dihydroindolyl, dihydrobenzodioxinyl, tetrahydroindolyl, tetrahydroindazolyl, tetrahydrobenzimidazolyl, tetrahydrobenzotriazolyl, tetrahydropyrrolopyridyl, tetrahydropyrazolopyridyl, tetrahydroimidazopyridyl, tetrahydrotriazolopyridyl, and tetrahydroquinolinyl groups. Heterocyclyl groups may be substituted or unsubstituted. Representative substituted heterocyclyl groups may be monosubstituted or substituted more than once, such as, but not limited to, pyridyl or morpholinyl groups, which are 2-, 3-, 4-, 5-, or 6-substituted, or disubstituted with various substituents such as those listed above.

Heteroaryl groups are aromatic ring compounds containing 5 or more ring members, of which, one or more is a heteroatom such as, but not limited to, N, O, and S. Heteroaryl groups include, but are not limited to, groups such as pyrrolyl, pyrazolyl, triazolyl, tetrazolyl, oxazolyl, isoxazolyl, thiazolyl, pyridinyl, pyridazinyl, pyrimidinyl, pyrazinyl, thiophenyl, benzothiophenyl, furanyl, benzofuranyl, indolyl, azaindolyl (pyrrolopyridinyl), indazolyl, benzimidazolyl, imidazopyridinyl (azabenzimidazolyl), pyrazolopyridinyl, triazolopyridinyl, benzotriazolyl, benzoxazolyl, benzothiazolyl, benzothiadiazolyl, imidazopyridinyl, isoxazolopyridinyl, thianaphthyl, purinyl, xanthinyl, adeninyl, guaninyl, quinolinyl, isoquinolinyl, tetrahydroquinolinyl, quinoxalinyl, and quinazolinyl groups. Heteroaryl groups include fused ring compounds in which all rings are aromatic such as indolyl groups and include fused ring compounds in which only one of the rings is aromatic, such as 2,3-dihydro indolyl groups. The phrase "heteroaryl groups" includes fused ring compounds. Heteroaryl groups may be substituted or unsubstituted. Representative substituted heteroaryl groups may be substituted one or more times with various substituents such as those listed above.

Heterocyclylalkyl groups are alkyl groups as defined above in which a hydrogen or carbon bond of an alkyl group is replaced with a bond to a heterocyclyl group as defined above. Heterocyclylalkyl groups may be substituted or unsubstituted. Substituted heterocyclylalkyl groups may be substituted at the alkyl, the heterocyclyl or both the alkyl and heterocyclyl portions of the group. Representative heterocyclyl alkyl groups include, but are not limited to, morpholin-4-yl-ethyl, furan-2-yl-methyl, imidazol-4-yl-methyl, pyridin-3-yl-methyl, tetrahydrofuran-2-yl-ethyl, and indol-2-yl-propyl. Representative substituted heterocyclylalkyl groups may be substituted one or more times with substituents such as those listed above.

Heteroarylalkyl groups are alkyl groups as defined above in which a hydrogen or carbon bond of an alkyl group is replaced with a bond to a heteroaryl group as defined above. Heteroarylalkyl groups may be substituted or unsubstituted. Substituted heteroarylalkyl groups may be substituted at the alkyl, the heteroaryl or both the alkyl and heteroaryl portions of the group. Representative substituted heteroarylalkyl groups may be substituted one or more times with substituents such as those listed above.

Groups described herein having two or more points of attachment (i.e., divalent, trivalent, or polyvalent) within the compound of the present technology are designated by use of the suffix, "ene." For example, divalent alkyl groups are alkylene groups, divalent aryl groups are arylene groups, divalent heteroaryl groups are divalent heteroarylene groups, and so forth. Substituted groups having a single point of attachment to the compound of the present technology are not referred to using the "ene" designation. Thus, for example, chloroethyl is not referred to herein as chloroethylene.

The terms "alkanoyl" and "alkanoyloxy" as used herein can refer, respectively, to —C(O)-alkyl groups and —O—C(O)-alkyl groups, each containing 2-5 carbon atoms. Similarly, "aryloyl" and "aryloyloxy" refer to —C(O)-aryl groups and —O—C(O)-aryl groups.

The terms "aryloxy" and "arylalkoxy" refer to, respectively, a substituted or unsubstituted aryl group bonded to an oxygen atom and a substituted or unsubstituted aralkyl group bonded to the oxygen atom at the alkyl. Examples include but are not limited to phenoxy, naphthyloxy, and benzyloxy. Aryloxy and arylalkoxy groups may each be may be substituted or unsubstituted. Representative substituted aryloxy and arylalkoxy groups may be substituted one or more times with substituents such as those listed above.

The term "carboxyl" as used herein refers to a —COOH group or its ionized form, —COO$^-$.

The term "ester" as used herein refers to —COOR$^{70}$ and —C(O)O-G groups. R$^{70}$ is a substituted or unsubstituted alkyl, cycloalkyl, alkenyl, alkynyl, aryl, aralkyl, heterocyclylalkyl or heterocyclyl group as defined herein. G is a carboxylate protecting group. Carboxylate protecting groups are well known to one of ordinary skill in the art. An extensive list of protecting groups for the carboxylate group functionality may be found in Protective Groups in Organic Synthesis, Greene, T. W.; Wuts, P. G. M., John Wiley & Sons, New York, N.Y., (3rd Edition, 1999) which can be added or removed using the procedures set forth therein and which is hereby incorporated by reference in its entirety and for any and all purposes as if fully set forth herein.

The term "amide" (or "amido") includes C- and N-amide groups, i.e., —C(O)NR$^{71}$R$^{72}$, and —NR$^{71}$C(O)R$^{72}$ groups, respectively. R$^{71}$ and R$^{72}$ are independently hydrogen, or a substituted or unsubstituted alkyl, alkenyl, alkynyl, cycloalkyl, aryl, aralkyl, heterocyclylalkyl or heterocyclyl group as defined herein. Amido groups therefore include but are not limited to carbamoyl groups (—C(O)NH$_2$) (also referred to as carboxamide) and formamide groups (—NHC(0)H). In some embodiments, the amide is —NR$^{71}$C(O)—(C$_{1-5}$ alkyl) and the group is termed "carbonylamino," and in others the amide is —NHC(O)-alkyl and the group is termed "alkanoylamino."

The term "nitrile" or "cyano" as used herein refers to the —CN group.

Urethane groups include N- and O-urethane groups, i.e., —NR$^{73}$C(O)OR$^{74}$ and —OC(O)NR$^{73}$R$^{74}$ groups, respectively. R$^{73}$ and R$^{74}$ are independently a substituted or unsubstituted alkyl, alkenyl, alkynyl, cycloalkyl, aryl, aralkyl, heterocyclylalkyl, or heterocyclyl group as defined herein. R$^{73}$ may also be H.

The term "amine" (or "amino") as used herein refers to —NR$^{75}$R$^{76}$ groups, wherein R$^{75}$ and R$^{76}$ are independently hydrogen, or a substituted or unsubstituted alkyl, alkenyl, alkynyl, cycloalkyl, aryl, aralkyl, heterocyclylalkyl or heterocyclyl group as defined herein. In some embodiments, the amine is alkylamino (i.e., —NHalkyl), dialkylamino (i.e., —N(alkyl)$_2$), arylamino (i.e., —NHaryl), or alkylarylamino (i.e., —N(alkyl)(aryl)). In other embodiments, the amine is NH$_2$, methylamino, dimethylamino, ethylamino, diethylamino, propylamino, isopropylamino, phenylamino, or benzylamino.

The term "sulfonamido" includes S- and N-sulfonamide groups, i.e., —SO$_2$NR$^{78}$R$^{79}$ and —NR$^{78}$SO$_2$R$^{79}$ groups, respectively. R$^{78}$ and R$^{79}$ are independently hydrogen, or a substituted or unsubstituted alkyl, alkenyl, alkynyl, cycloalkyl, aryl, aralkyl, heterocyclylalkyl, or heterocyclyl group as defined herein. Sulfonamido groups therefore include but are not limited to sulfamoyl groups (—SO$_2$NH$_2$). In some embodiments herein, the sulfonamido is —NHSO$_2$-alkyl and is referred to as the "alkylsulfonylamino" group.

The term "thiol" refers to —SH groups, while "sulfides" include —SR$^{80}$ groups, "sulfoxides" include —S(O)R$^{81}$ groups, "sulfones" include —SO$_2$R$^{82}$ groups, and "sulfonyls" include —SO$_2$OR$^{83}$. R$^{80}$, R$^{81}$, R$^{82}$, and R$^{83}$ are each independently a substituted or unsubstituted alkyl, cycloalkyl, alkenyl, alkynyl, aryl aralkyl, heterocyclyl or heterocyclylalkyl group as defined herein. In some embodiments the sulfide is an alkylthio group, —S-alkyl.

The term "urea" refers to —NR$^{84}$—C(O)—NR$^{85}$R$^{86}$ groups. R$^{84}$, R$^{85}$, and R$^{86}$ groups are independently hydrogen, or a substituted or unsubstituted alkyl, alkenyl, alkynyl, cycloalkyl, aryl, aralkyl, heterocyclyl, or heterocyclylalkyl group as defined herein.

The term "amidine" refers to —C(NR$^{87}$)NR$^{88}$R$^{89}$ and —NR$^{87}$C(NR$^{88}$)R$^{89}$, wherein R$^{87}$, R$^{88}$, and R$^{89}$ are each independently hydrogen, or a substituted or unsubstituted alkyl, cycloalkyl, alkenyl, alkynyl, aryl aralkyl, heterocyclyl or heterocyclylalkyl group as defined herein.

The term "guanidine" refers to —NR$^{90}$C(NR$^{91}$)NR$^{92}$R$^{93}$, wherein R$^{90}$, R$^{91}$, R$^{92}$ and R$^{93}$ are each independently hydrogen, or a substituted or unsubstituted alkyl, cycloalkyl, alkenyl, alkynyl, aryl aralkyl, heterocyclyl or heterocyclylalkyl group as defined herein.

The term "enamine" refers to —C(R$^{94}$)=C(R$^{95}$)NR$^{96}$R$^{97}$ and —NR$^{94}$C(R$^{95}$)=C(R$^{96}$)R$^{97}$, wherein R$^{94}$, R$^{95}$, R$^{96}$ and R$^{97}$ are each independently hydrogen, a substituted or unsubstituted alkyl, cycloalkyl, alkenyl, alkynyl, aryl aralkyl, heterocyclyl or heterocyclylalkyl group as defined herein.

The term "halogen" or "halo" as used herein refers to bromine, chlorine, fluorine, or iodine. In some embodiments, the halogen is fluorine. In other embodiments, the halogen is chlorine or bromine.

The term "hydroxyl" as used herein can refer to —OH or its ionized form, —O$^-$. A "hydroxyalkyl" group is a hydroxyl-substituted alkyl group, such as HO—CH$_2$—.

The term "imide" refers to —C(O)NR$^{98}$C(O)R$^{99}$, wherein R$^{98}$ and R$^{99}$ are each independently hydrogen, or a substituted or unsubstituted alkyl, cycloalkyl, alkenyl, alkynyl, aryl aralkyl, heterocyclyl or heterocyclylalkyl group as defined herein.

The term "imine" refers to —CR$^{100}$(NR$^{101}$) and —N(CR$^{100}$R$^{101}$) groups, wherein R$^{100}$ and R$^{101}$ are each independently hydrogen or a substituted or unsubstituted alkyl, cycloalkyl, alkenyl, alkynyl, aryl aralkyl, heterocyclyl or heterocyclylalkyl group as defined herein, with the proviso that R$^{100}$ and R$^{101}$ are not both simultaneously hydrogen.

The term "nitro" as used herein refers to an —NO$_2$ group.

The term "trifluoromethyl" as used herein refers to —CF$_3$.

The term "trifluoromethoxy" as used herein refers to —OCF$_3$.

The term "azido" refers to —N$_3$.

The term "trialkyl ammonium" refers to a —N(alkyl)$_3$ group. A trialkylammonium group is positively charged and thus typically has an associated anion, such as halogen anion.

The term "isocyano" refers to —NC.

The term "isothiocyano" refers to —NCS.

The term "amino acid" refers to any natural or unnaturally occurring alpha-amino acids. Stereochemistry at the alpha carbon may be L, D, or a mixture there of. Except where indicated as encompassing both D and/or L or where expressly defined as D, proteinogenic amino acids have L stereochemistry at the alpha carbon.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges which can be subsequently broken down into subranges as discussed above. Finally, as will be understood by one skilled in the art, a range includes each individual member. Thus, for example, a group having 1-3 atoms refers to groups having 1, 2, or 3 atoms. Similarly, a group having 1-5 atoms refers to groups having 1, 2, 3, 4, or 5 atoms, and so forth.

In one aspect, the present technology provides a system for monitoring bacterial production/release of membrane-lytic toxins, including, e.g., production/release controlled by quorum-sensing in bacteria. The system includes bacteria that release at least one membrane-lytic toxin. In any embodiments, the bacteria may release at least one membrane-lytic toxin when, e.g., the bacteria are at a quorum-sensing density. The system further includes synthetic lipid vesicles comprising an environmentally sensitive indicator, wherein the synthetic lipid vesicles release the environmentally sensitive indicator in the presence of an effective amount of the membrane-lytic toxins. The system further includes a growth medium, wherein the bacteria and synthetic lipid vesicles are in contact with the growth medium.

The present system utilizes synthetic lipid vesicles that are not naturally occurring. They may be unilamellar or multilamellar. The synthetic lipid vesicles may have an average hydrodynamic diameter of 15 to 200 nm, such as 15, 20, 30, 40, 50, 60, 70, 80, 90, 100, 110, 120, 130, 140, 150, 160, 170, 180, 190, or 200 nm or a range between and including any two of the foregoing values, e.g., 130-180 nm.

The synthetic lipid vesicles may include one or more phospholipids. Optionally, the synthetic lipid vesicles may include a sterol, e.g., cholesterol. In any embodiments, the one or more unsaturated phospholipids may include one or more of 1,2-dioleoyl-sn-glycerol phosphocholine (DOPC), 1,2-dipalmitoyl-sn-glycerol-3-phosphocholine (DPPC), or 1,2-dipalmitoyl-sn-glycerol-3-phosphoethanolamine (DPPE). In any embodiments, the synthetic lipid vesicles include DOPC and cholesterol. In any embodiments, the synthetic lipid vesicles may include 60-80 mol % DOPC and 20-40 mol % cholesterol. In any embodiments, the synthetic lipid vesicles may include DPPC, DPPE, and cholesterol, e.g., 57-79 mol % DPPC, 1-3 mol % DPPE, and 20-40 mol % cholesterol. In any embodiments, the synthetic lipid vesicles are not cross-linked. In certain embodiments, the synthetic lipid vesicles include cross-links between some (but not all) of the lipids in the vesicles.

The present system utilizes an environmentally sensitive indicator (e.g., a dye or particles), i.e., an indicator that undergoes or causes a readily detectable change depending on whether it is inside or outside the synthetic lipid vesicles, thereby allowing the integrity of the vesicles to be assessed. For example, an environmentally sensitive indicator may be an environmentally sensitive dye or environmentally sensitive particles that, in response to its/their environment, may change in color, absorption, emission, or intensity of the light signal produced. They may, e.g., be pH-sensitive, self-quenching, or redox sensitive dyes. In any embodiments, the environmentally sensitive indicator may be a colorimetric, fluorescent, chemiluminescent, or phosphorescent dye. In any embodiments, the environmentally sensitive dye may be a self-quenching fluorescent dye. While the present system may include synthetic lipid vesicles that release (leak) a small amount (i.e., a background amount) of environmentally sensitive dye over time, e.g., a 24 or 48 hour period, the amount does not substantially interfere with assays using the system. Generally, the synthetic lipid vesicles do not release a significant amount (e.g., a detectable, interfering amount) of the environmentally sensitive indicator (e.g., dye or particles) in the absence of an effective amount of membrane-lytic toxins. Non-limiting examples of small molecule dyes include those selected from the general classes of calcein, cyanine, ALEXA FLUOR (sulfonated dyes, including sulfonated fluorescein, coumarins, cyanine and rhodamines), azo, fluorescein, rhodamine, BODIPY, coumarin, dansyl, or pyrene dyes. Non-limiting examples of protein-based dyes include those selected from green fluorescent protein (GFP), yellow fluorescent protein (YFP), mCherry, and conjugates/split variants/close variants thereof.

The present system may be used with any bacteria that engages in quorum sensing and/or releases membrane-lytic toxins. In any embodiments, the bacteria may be selected from *Acinetobacter, Bacillus, Burkholderia, Clostridia, Enterococcus, Escherichia, Listeria, Pseudomonas, Staphylococcus, Streptococcus, Salmonella* or *Vibrio*. In any embodiments, the bacteria may be selected from the group consisting of *B. anthracis, B. cereus, E. faecalis, E. coli, L. monocytogenes, S. aureus, S. epidermidis, S. pyogenes, P. aeruginosa, P. chlororaphis, P. plantarii, P. putida, P. fluorescens,* and *B. thailandensis*. In any embodiments, the bacteria are *S. aureus* or *P. aeruginosa*.

In the system, the bacteria and synthetic lipid vesicles are in contact with a growth medium. In any embodiments, the bacteria and the synthetic lipid vesicles may be suspended in an aqueous growth medium. Alternatively or in addition, the bacteria and/or vesicles may be suspended in or attached to a solid medium, e.g., suspended in or attached to a gel. In any embodiments the solid medium may be, e.g., agar or a plastic surface such as a well in a plastic microtiter plate. A variety of growth media suitable for the bacteria may be used in the system, so long as the bacteria may release the at least one membrane-lytic toxin. For example, quorum sensing bacteria should reach quorum-sensing density in a reasonable amount of time (e.g., 4-24 hours) in the growth medium. Such growth media are known in the art. Non-limiting examples of aqueous growth media that may be used, including nutrient rich media like brain heart infusion (BHI) medium or tryptic soy broth (TSB) with, e.g., *S. aureus, S. epidermidis, B. anthracis, B. cereus,* and *L. monocytogenes,* and minimal media like Luria-Bertani (LB) medium and M9 medium with, e.g., *P. aeruginosa, P. chlororaphis, P. plantarii, P. putida, P. fluorescens, B. thailandensis,* and *E. coli*.

The system described herein may also include a test compound to determine whether the compound is capable of modulating bacterial production and/or release of membrane-lytic toxins and/or quorum sensing, and if so, how strongly. For example, in an initial screen such as a high throughput screen, the test compound may be present at a fairly high concentration such as 10 uM, but other concentrations may be used (e.g., 1, 2, 3, 4, 5, 6, 7, 8, 9, 10, 15, 20, 30, 40, 50, 75, or 100 uM or a range between and including any two of the foregoing values). Lower concentrations of test compounds may also be used for more potent compounds (e.g. 100, 200, 300, 400, 500, 600, 700, 800, 900 nM or a range between and including any two of the foregoing values). In any embodiments, the test compound is an inhibitor of quorum sensing. In any embodiments, the test compound potentiates quorum sensing by the bacteria.

In another aspect the present technology provides an assay of bacterial quorum sensing comprising culturing the bacteria in any of the systems described herein to a quorum-sensing density in the presence or absence of a test compound, and detecting a signal or absence thereof during and/or after the bacterial culture has released the effective amount of at least one membrane-lytic toxin. In any embodiments, the assay is repeated at different concentrations of test compound (e.g., 2, 3, 4, 5, or more times at different concentrations of the test compound). In any embodiments, the assay is part of a high through-put screen of two or more test compounds (e.g., 2, 10, 100, 500, 1,000, 5,000, 10,000, 25,000, 50,000, 100,000, 200,000 or more compounds). In any embodiments the assay is a continuous assay. For example, the change in signal intensity resulting from the dye is measured over a fixed time period. Any suitable time-period may be used, e.g., 1, 2, 3, 4, 5, 10, 20, 30, 40, or 50 minutes, or 1, 1.5, 2, 3, 4, 5, 6, 8, 10, 12, 14, 16, 18, 20, or 24 hours, or any time in between and including any two of the foregoing time periods. In any embodiments, the assay is carried out in a microtiter plate with, e.g., 96, 384, or 1536 wells.

In still another aspect, the present technology provides a method of assaying production/release of membrane-lytic toxins by any bacteria. The method includes culturing the bacteria in any of the systems described herein for a period of time during which (in the absence of a test compound or inhibitor), an effective amount of at least one membrane-lytic toxin is released by the bacteria, and detecting a signal or absence thereof during and/or after the bacterial culture has released the effective amount of at least one membrane-lytic toxin. In any embodiments, the culturing is carried out in the presence of a test compound. In any embodiments, the assay is repeated at different concentrations of test compound (e.g., 2, 3, 4, 5 or more times at different concentrations of the test compound). In any embodiments, the assay is part of a high through-put screen of two or more test compounds (e.g., 2, 10, 100, 500, 1,000, 5,000, 10,000, 25,000, 50,000, 100,000, 200,000 or more compounds). In any embodiments the assay is a continuous assay. For example, the change in signal intensity resulting from the dye is measured over a fixed time period. In any embodiments, the assay is carried out in a microtiter plate with, e.g., 96, 384, or 1536 wells. In any embodiments, the bacteria may be any of those described herein. In any embodiments, the bacteria may be quorum sensing bacteria, e.g., any of the quorum sensing bacteria described herein.

In yet another aspect, the present technology provides a compound having the structure of Formula I or Formula II:

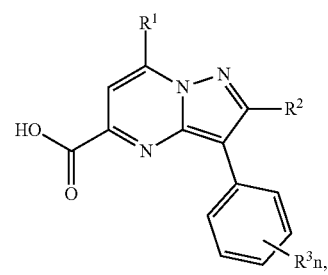

-continued

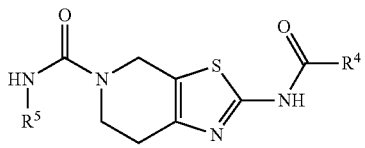

II and/or a tautomer thereof and/or a pharmaceutically acceptable salt thereof,
wherein
$R^1$ is OH (or its oxo tautomer), or a substituted or unsubstituted alkyl, cycloalkyl, or cycloalkylalkyl group;
$R^2$ is H, halogen, OH, $NO_2$, or a substituted or unsubstituted alkyl, cycloalkyl or cycloalkylalkyl group;
$R^3$ is a halogen, CN, $NO_2$, or a substituted or unsubstituted alkyl, cycloalkyl, or cycloalkylalkyl group; and
$R^4$ is $OR^a$, $NHR^a$, or a substituted or unsubstituted alkyl, cycloalkyl, cycloalkylalkyl, aryl, aralkyl, heteroaryl, or heteroarylalkyl group;
$R^5$ is a substituted or unsubstituted alkyl, cycloalkyl, cycloalkylalkyl, aryl, aralkyl, heteroaryl, or heteroarylalkyl group;
$R^a$ is substituted or unsubstituted alkyl, cycloalkyl, cycloalkylalkyl, aryl, aralkyl, heteroaryl, or heteroarylalkyl group; and
n is 1, 2, 3, 4 or 5.

In any embodiments, one or more compounds may be excluded from the compounds of Formula I or Formula II. For example, in any embodiments, the compound is not 7-isopropyl-2-methyl-3-phenylpyrazolo[1,5-a]pyrimidine-5-carboxylic acid, and is not N-(3-chlorophenyl)-2-(thiophene-3-carboxamido)-6,7-dihydrothiazolo[5,4-c]pyridine-5(4H)-carboxamide.

In any embodiments, the compound is the compound of Formula I. In any embodiments, $R^1$ may be a substituted or unsubstituted alkyl or cycloalkyl, group. In any embodiments, $R^1$ may be an unsubstituted $C_{1-6}$ alkyl group or an unsubstituted $C_{3-6}$ cycloalkyl group. In any embodiments, $R^1$ may be a methyl, ethyl, isopropyl, n-propyl, t-butyl, cyclopropyl, cyclobutyl, or cyclopentyl group. In any embodiments, $R^2$ may be halogen, OH, $NO_2$, or a substituted or unsubstituted alkyl or cycloalkyl group. In any embodiments, $R^2$ is fluoro, chloro, OH, $NO_2$, or an unsubstituted methyl, ethyl, isopropyl, butyl, cyclopropyl, or cyclobutyl group. In any embodiments, $R^3$ is halogen, $NO_2$, or a substituted or unsubstituted alkyl or cycloalkyl group. In any embodiments, $R^3$ is F, Cl, $NO_2$, or an unsubstituted $C_{1-6}$ alkyl group, e.g., methyl, ethyl, propyl or butyl.

In any embodiments, the compound is the compound of Formula II. In any embodiments, $R^4$ may be a substituted or unsubstituted cycloalkyl, aryl, or heteroaryl group. In any embodiments, $R^4$ may be cyclopentyl, cyclohexyl, phenyl, thiophenyl, furanyl, each of which is optionally substituted with one or more halogen or a substituted or unsubstituted alkyl group. $R^4$ may be optionally substituted with 1, 2, or 3 substituents. In any embodiments, the substituents may be selected from the group consisting of F, Cl, and an unsubstituted $C_{1-6}$ alkyl group. In any embodiments, $R^5$ may be a substituted or unsubstituted cycloalkyl, aryl, or heteroaryl group. In any embodiments, $R^5$ may be cyclopentyl, cyclohexyl, phenyl, thiophenyl, furanyl, each of which is optionally substituted with one or more halogen or a substituted or unsubstituted alkyl group, $R^5$ may be optionally substituted with 1, 2, or 3 substituents, e.g., substituents selected from the group consisting of F, Cl, and an unsubstituted $C_{1-6}$ alkyl group.

In another aspect, the present technology provides a method of modulating release of a membrane-lytic toxin by bacteria comprising contacting the bacteria with an effective amount of any compound as described herein (e.g., a compound of Formula I or II). In any embodiments, the bacteria release the membrane-lytic toxin upon reaching a quorum-sensing density. In such embodiments, the method may be used to modulate quorum sensing. The compound selected for use may potentiate (activate) quorum sensing or may inhibit quorum sensing. In any embodiments, the compound is a quorum sensing inhibitor and the method inhibits quorum sensing. In any embodiments, the method may be carried out in vitro.

In another aspect, the present technology provides a method of inhibiting quorum sensing by bacteria and/or treating a bacterial infection caused by quorum sensing bacteria (or by bacteria that release a membrane-lytic toxin), including without limitation, any bacteria described herein. The method includes administering an effective amount of a compound of Formula I or Formula II to a subject in need thereof. In any embodiments, the compound of Formula I or Formula II may be any of those described herein. The subject may be a human or a non-human animal. Thus, the subject may be selected from a variety of non-human animals such as domestic pets (cats, dogs, gerbils, hamsters, hedgehogs, birds, and the like), livestock such as poultry, ruminants, and the like. In any embodiments, the subject may be selected from the group consisting of cattle, sheep, buffalo and goats. The compound may be administered by any route disclosed herein, including systemically, or to treat skin infections, topically. In any embodiments, the methods further include administering an effective amount of a second therapeutic agent such as a different class of antibiotics, e.g., beta lactams (e.g., penicillins, carbapenems, cephalosporins, and monobactams), aminoglycosides (e.g., streptomycin, kanamycin, neomycin, and tobramycin), fluoroquinolones, glycopeptides (e.g., vancomycin), macrolides (e.g., erythromycin, azithromycin), oxazolidinones (e.g., linezolid, tedizolid), rifamycins, sulfonamides, and tetracylines (e.g., doxycycline, tetracycline). Thus, the compound of the present technology may be administered with an effective amount of the second therapeutic agent separately, sequentially, or simultaneously. In any embodiments of the methods, the QS may be *Bacillus, Burkholderia, Enterococcus, Escherichia, Listeria, Pseudomonas, Staphylococcus, Streptococcus,* or *Vibrio*. In any embodiments of the methods, the bacteria may be selected from the group consisting of *B. anthracis, B. cereus, E. faecalis, E. coli, L. monocytogenes, S. aureus, S. epidermidis, S. pyogenes, P. aeruginosa, P. chlororaphis, P. plantarii, P. putida, P. fluorescens,* and *B. thailandensis*. In any embodiments of the methods, the bacteria may be *S. aureus* or *P. aeruginosa*. In any embodiments of the methods, the compound may be a compound of Formula I or a compound of Formula II, or any compound thereof, described herein.

The present technology provides compositions including any of the compounds disclosed herein and a carrier and/or excipient. Thus in any embodiments, the compositions are pharmaceutical compositions and medicaments comprising any one of the embodiments of the compounds disclosed herein and one or more pharmaceutically acceptable carriers and/or excipients. The compositions may be used in the methods and treatments described herein. Thus, in any embodiments, the compositions may include an amount of the compound effective for inhibiting quorum sensing, wherein the carrier and/or excipients are pharmaceutically acceptable, and the composition is a pharmaceutical composition. In any embodiments, the pharmaceutical composition may include an effective amount of any of one of the embodiments of the compounds or compositions disclosed herein for modulating quorum sensing in bacteria, e.g., in Gram-positive bacteria such as *S. aureus* and Gram-negative bacteria such as *P. aeruginosa*.

The compositions described herein can be formulated for use on surfaces (e.g., as disinfectants), including as aqueous solutions or suspensions, non-aqueous solutions or suspensions, or creams, pastes, gels or the like. Thus, the compositions may be sprayed, cast or rubbed on a surface, or applied with a cloth, sponge, roller, or any suitable applicator known in the art. The compositions may formulated as a coating with suitable polymers and other agents to provide long lasting antibacterial activity over days (e.g., 1, 2, 3, 4, 5, or 6), weeks (e.g., 1, 2, or 3), months (e.g., 1-11) or even up to a year after application to a surface. The effective amount of a compound described herein may be from 0.0001 wt % to 10 wt % based on the total weight of the composition, depending on the intended use and delivery route. In any embodiments, the effective amount may be 0.0001 wt %, 0.0005 wt %, 0.001 wt %, 0.005 wt %, 0.01 wt %, 0.05 wt %, 0.1 wt %, 0.5 wt %, 1 wt %, 2 wt %, 5 wt %, 10 wt % or a range between or including any two of the foregoing values. For example, in any embodiments, the effective amount may be from 0.01 wt % to 1 wt %.

The compositions described herein can also be formulated for various routes of administration to treat or prevent infection, for example, by oral, parenteral, topical, injection, rectal, nasal, vaginal administration, or via implanted reservoir (or may simply be part of a coating on the surface of the implant in contact with tissue). Parenteral or systemic administration includes, but is not limited to, subcutaneous, intravenous, intraperitoneal, and intramuscular injections. The following dosage forms are given by way of example and should not be construed as limiting the instant present technology.

For oral, buccal, and sublingual administration, powders, suspensions, granules, tablets, pills, capsules, gelcaps, and caplets are acceptable as solid dosage forms. These can be prepared, for example, by mixing one or more compounds disclosed herein, or pharmaceutically acceptable salts or stereoisomers thereof, with at least one additive such as a starch or other additive. Suitable additives are sucrose, lactose, cellulose sugar, mannitol, maltitol, dextran, starch, agar, alginates, chitins, chitosans, pectins, tragacanth gum, gum arabic, gelatins, collagens, casein, albumin, synthetic or semi-synthetic polymers or glycerides. Optionally, oral dosage forms can contain other ingredients to aid in administration, such as an inactive diluent, or lubricants such as magnesium stearate, or preservatives such as paraben or sorbic acid, or anti-oxidants such as ascorbic acid, tocopherol or cysteine, a disintegrating agent, binders, thickeners, buffers, sweeteners, flavoring agents or perfuming agents. Tablets and pills may be further treated with suitable coating materials known in the art.

Liquid dosage forms for oral administration may be in the form of pharmaceutically acceptable emulsions, syrups, elixirs, suspensions, and solutions, which may contain an inactive diluent, such as water. Pharmaceutical formulations and medicaments may be prepared as liquid suspensions or solutions using a sterile liquid, such as, but not limited to, an oil, water, an alcohol, and combinations of these. Pharmaceutically suitable surfactants, suspending agents, emulsifying agents, may be added for oral or parenteral administration.

As noted above, suspensions may include oils. Such oils include, but are not limited to, peanut oil, sesame oil, cottonseed oil, corn oil and olive oil. Suspension preparation may also contain esters of fatty acids such as ethyl oleate, isopropyl myristate, fatty acid glycerides and acetylated fatty acid glycerides. Suspension formulations may include alcohols, such as, but not limited to, ethanol, isopropyl alcohol, hexadecyl alcohol, glycerol and propylene glycol. Ethers, such as but not limited to, poly(ethyleneglycol), petroleum hydrocarbons such as mineral oil and petrolatum; and water may also be used in suspension formulations.

Injectable dosage forms generally include solutions or aqueous suspensions which may be prepared using a suitable dispersant or wetting agent and a suspending agent so long as such agents do not interfere with the activity of the drugs described herein. Injectable forms may be prepared with acceptable solvents or vehicles including, but not limited to sterilized water, Ringer's solution, 5% dextrose, or an isotonic aqueous saline solution. Alternatively, sterile oils may be employed as solvents or suspending agents. Typically, the oil or fatty acid is non-volatile, including natural or synthetic oils, fatty acids, mono-, di- or tri-glycerides.

For injection, the pharmaceutical formulation and/or medicament may be a powder suitable for reconstitution with an appropriate solution as described above. Examples of these include, but are not limited to, freeze dried, rotary dried or spray dried powders, amorphous powders, granules, precipitates, or particulates. For injection, the formulations may optionally contain stabilizers, pH modifiers, surfactants, bioavailability modifiers and combinations of these.

Compounds of the present technology also may be formulated as a composition for topical administration (e.g., creams, ointments, gels, foams, transdermal patch, wound dressing, and the like). These formulations may contain various excipients known to those skilled in the art. Suitable excipients may include, but are not limited to, cetyl esters wax, cetyl alcohol, white wax, glyceryl monostearate, propylene glycol monostearate, methyl stearate, benzyl alcohol, sodium lauryl sulfate, glycerin, mineral oil, water, carbomer, ethyl alcohol, acrylate adhesives, polyisobutylene adhesives, and silicone adhesives.

Dosage units for rectal administration may be prepared in the form of suppositories which may contain the composition of matter in a mixture with a neutral fat base, or they may be prepared in the form of gelatin-rectal capsules which contain the active substance in a mixture with a vegetable oil or paraffin oil.

Compounds of the present technology may be administered to the lungs by inhalation through the nose or mouth. Suitable pharmaceutical formulations for inhalation include solutions, sprays, dry powders, or aerosols containing any appropriate solvents and optionally other compounds such as, but not limited to, stabilizers, antimicrobial agents, antioxidants, pH modifiers, surfactants, bioavailability modifiers and combinations of these. Formulations for inhalation administration contain as excipients, for example, lactose, polyoxyethylene-9-lauryl ether, glycocholate and deoxycholate. Aqueous and nonaqueous aerosols are typically used for delivery of inventive compounds by inhalation.

Ordinarily, an aqueous aerosol is made by formulating an aqueous solution or suspension of the compound together with conventional pharmaceutically acceptable carriers and stabilizers. The carriers and stabilizers vary with the requirements of the particular compound, but typically include nonionic surfactants (Tweens, Pluronics, or polyethylene glycol), innocuous proteins like serum albumin, sorbitan esters, oleic acid, lecithin, amino acids such as glycine, buffers, salts, sugars or sugar alcohols. Aerosols generally are prepared from isotonic solutions. A nonaqueous suspension (e.g., in a fluorocarbon propellant) can also be used to deliver compounds of the present technology.

Aerosols containing compounds for use according to the present technology are conveniently delivered using an inhaler, atomizer, pressurized pack or a nebulizer and a suitable propellant, e.g., without limitation, pressurized dichlorodifluoromethane, trichlorofluoromethane, dichlorotetrafluoroethane, nitrogen, air, or carbon dioxide. In the case of a pressurized aerosol, the dosage unit may be controlled by providing a valve to deliver a metered amount. Capsules and cartridges of, for example, gelatin for use in an inhaler or insufflator may be formulated containing a powder mix of the compound and a suitable powder base such as lactose or starch. Delivery of aerosols of the present technology using sonic nebulizers is advantageous because nebulizers minimize exposure of the agent to shear, which can result in degradation of the compound.

For nasal administration, the pharmaceutical formulations and medicaments may be a spray, nasal drops or aerosol containing an appropriate solvent(s) and optionally other compounds such as, but not limited to, stabilizers, antimicrobial agents, antioxidants, pH modifiers, surfactants, bioavailability modifiers and combinations of these. For administration in the form of nasal drops, the compounds may be formulated in oily solutions or as a gel. For administration of nasal aerosol, any suitable propellant may be used including compressed air, nitrogen, carbon dioxide, or a hydrocarbon based low boiling solvent.

Besides those representative dosage forms described above, pharmaceutically acceptable excipients and carriers are generally known to those skilled in the art and are thus included in the instant present technology. Such excipients and carriers are described, for example, in "Remingtons Pharmaceutical Sciences" Mack Pub. Co., New Jersey (1991), which is incorporated herein by reference. Thus, the present technology provides a pharmaceutical composition comprising any polymer-drug conjugate as described herein and a pharmaceutically acceptable carrier or excipient.

Specific dosages for therapy may be adjusted depending on conditions of disease, the age, body weight, general health conditions, sex, and diet of the subject, dose intervals, administration routes, excretion rate, and combinations of compounds. Any of the above dosage forms containing effective amounts are well within the bounds of routine experimentation and therefore, well within the scope of the instant present technology.

A therapeutically effective amount of a compound of the present technology may vary depending upon the route of administration and dosage form. Effective amounts of such compounds typically fall in the range of about 0.01 up to about 100 mg/kg/day, or about 0.05 to about 50 mg/kg/day, and may fall in the range of about 0.1 up to 5 mg/kg/day. Typically, the compound or compounds of the instant technology are selected to provide a formulation that exhibits a high therapeutic index. The therapeutic index is the dose ratio between toxic and therapeutic effects and can be expressed as the ratio between $LD_{50}$ and $ED_{50}$. The $LD_{50}$ is the dose lethal to 50% of the population and the $ED_{50}$ is the dose therapeutically effective in 50% of the population. The $LD_{50}$ and $ED_{50}$ are determined by standard pharmaceutical procedures in animal cell cultures or experimental animals.

Effective amounts of compounds of the present technology may be administered by various routes as described herein and may be given all at once or take place over a period of time including but not limited to 5 minutes, 10 minutes, 20 minutes, 30 minutes, 45 minutes, 1 hour, 2 hours, 3 hours, 5 hours, 10 hours, 12, hours, 15 hours, 20 hours, 24 hours or a range between and including any of the foregoing values. The frequency of administration may vary, for example, once or twice per day, per 2 days, per 3 days, per week, per 10 days, per 2 weeks, every other day, or a range between and including any of the foregoing frequencies. Alternatively, the compositions may be administered once per day on 2, 3, 4, 5, 6 or 7 consecutive days. A complete regimen may thus be completed in only a few days or over the course of 1, 2, 3, 4, 5, 6 or more weeks.

In another aspect, the present technology provides methods for reducing virulence by quorum sensing bacteria. The methods include contacting the quorum sensing bacteria (i.e., any described herein) with an effective amount of any compound disclosed herein.

In another aspect, the present technology provides methods of inhibiting biofilm formation by quorum sensing bacteria on a surface comprising contacting the bacteria (including, but not limited to any of the bacteria described herein, e.g., *S. aureus* and *P. aeruginosa*) with an effective amount of a compound disclosed herein. In any embodiments, the methods further include applying the effective amount of the compound to the surface. The surface includes any one on which bacteria may grow and form biofilms. In any embodiments, the surface may be a food surface, a food storage or preparation surface, or a food packaging surface. For example, the food surface may be the surface of a fruit or vegetable, an animal carcass, meat, poultry, or fish, or even sauces and condiments. Food may also include animal food, such as silage. Food storage and preparation surfaces may include but are not limited to counter tops, shelves, cupboards, racks, refrigerators, stove tops, ovens, bowls, utensils, cups, plates, boards, tables, and the surfaces of other food processing equipment (e.g., mixers, blenders, vats, shredders, grinders, valves, piping, pumps, screens, slicers, separators, forming equipment, and the like). Hence, there are also provided methods of preventing food-borne listeriosis including applying a composition comprising an effective amount of a compound as described herein to a food surface, a food-preparation surface, or a food packaging surface.

The examples herein are provided to illustrate advantages of the present technology and to further assist a person of ordinary skill in the art with preparing or using the drugs of the present technology. To the extent that the compositions include ionizable components, salts such as pharmaceutically acceptable salts of such components may also be used. The examples herein are also presented in order to more fully illustrate certain aspects of the present technology. The examples should in no way be construed as limiting the scope of the present technology, as defined by the appended claims. The examples can include or incorporate any of the variations, aspects or aspects of the present technology described above. The variations, aspects or aspects described above may also further each include or incorporate the variations of any or all other variations, aspects or aspects of the present technology

EXAMPLES

Materials and General Methods

Materials. 1,2-Dioleoyl-sn-glycerol-3-phosphocholine (DOPC), 1,2-dipalmitoyl-sn-glycerol-3-phosphocholine (DPPC), cholesterol, filter supports, and a Mini extruder were purchased from Avanti Polar Lipids. 1,2-Dipalmitoyl-sn-glycerol-3-phosphoethanolamine (DPPE), dimethyl sulfoxideDMSO), sodium hydroxide (NaOH), hydrochloric acid (HCl), sodium chloride (NaCl), triethylphosphine oxide, deuterium oxide (D2O), calcein, Triton X-100, and Sephadex-G50 column size exclusion chromatography beads were purchased from Sigma. Isopropanol (iPrOH) and tris-base were acquired from Fisher Scientific. Rhamnolipids, 90% pure (commercial mixture of glycolipids isolated from P. aeruginosa) were obtained from AGAE Technologies (Corvallis, Oreg.). The small-molecule agr inhibitor savirin was purchased from AK Scientific. Polycarbonate extruder filters (100 nm) were purchased from Millipore. Ethylenediaminetetraacetic acid (EDTA) was acquired from Acros Organics. Concentrated phosphate buffered saline (PBS) solution (10×) was purchased from Dot Scientific. Luria-Bertani (LB) medium was obtained from Research Products International. Brain heart infusion (BHI) medium was acquired from Teknova. The phenol-soluble modulin PSMa3 was a kind gift from Prof. Samuel H. Gellman (UW-Madison, Madison, WI). Deionization of distilled water was performed using a Milli-Q system yielding water with a resistivity of 18.2 MΩ. All materials were used as received without further purification unless otherwise specified.

Bacterial strains and culture. All bacteria were grown at 37° C. with 200 rpm shaking unless otherwise specified. The strains and plasmids used in this work and their sources are listed in Table 1. S. aureus and P. aeruginosa were grown in BHI medium and LB medium, respectively. S. aureus AH1677 (with an agr-YFP reporter plasmid) and P. aeruginosa PAO1-PGSC (with a plasI-LVAgfp reporter plasmid) were used as QS transcriptional reporters and grown with 10 μg/mL chloramphenicol and 300 μg/mL carbenicillin, respectively. All other strains were grown without supplemental antibiotic. S. aureus RN6390b and P. aeruginosa PAO1-PGSC were used as WT strains in vesicle lysis experiments, while S. aureus RN9222 and P. aeruginosa PAO-JG35 were used as QS mutants. RN9222 was grown without antibiotic as it was not used as a reporter strain (i.e., it served only as QS mutant).

TABLE 1

Bacterial strains and plasmids used in the Examples

| | Description | Reference or Source |
|---|---|---|
| *Staphylococcus aureus* | | |
| RN6390 | Wild-type, agr group I (NTCC 8325 cured of prophages)[1] | Novick (1967) |
| RN9222 | RN6911 with pRN7062, QS mutant | Lyon et al. (2000) |
| RN6911 | agr::tetM(agr-null), fromRN6390 | Novick et al. (1993) |
| AH1677 | USA300 LAC with pDB59 | Kirchdoerfer et al. (2011) |
| *Pseudomonas aeruginosa* | | |
| PAO1-PGSC | Wild-type | Pseudomonas Genetic Stock Center |
| PAO-JG35 | ΔlasR::Tc$^R$ ΔrhlR, Tc$^R$, from PAO1-PGSC, QS mutant | Gerdt and Blackwell (2014) |
| Plasmids | | |
| pDB59 | P3-yfp$_{10B}$ transcriptional fusion, Cm$^R$ | Yarwood et al. (2004) |
| pRN7062 | Contains agrCA and P3-blaZ transcriptional fusion, Erm$^R$ | Lyon et al. (2000) |
| plasI-LVAgfp | plasI-LVAgfp transcriptional fusion, Amp$^R$ | De Kievit et al. 2001 |

Compound handling and preparation. OdDHL and BHL (Hodgkinson et al., 2011), S. aureus AIP and peptide derivatives 1-5 (Tal-Gan et al., 2013, Tal-Gan et al., 2016, Vasquez and Blackwell, 2019), and compounds 7-9 (Welsh and Blackwell, 2016a, Boursier et al., 2018, Manson et al., 2020) were synthesized using previously described methods. PQS and compound 6 were purchased from Millipore Sigma and AK Scientific respectively. Compounds were stored dry at −20° C. until needed and then dissolved in DMSO. DMSO stock solutions were prepared at concentrations that varied with compound potency and apparent solubility. Final in-well compound concentrations for 96-well vesicle lysis assays, unless noted otherwise, were: 10 μM for AIP, OdDHL, and PQS; 1 mM for BHL; 100 nM for 1-4; 10 μM for 5; 20 μM for 6; 100 μM for 7 and 8; and 200 μM for 9.

NMR quantification of concentrations of phospholipids in vesicles. The concentration of phospholipids in stock solutions of vesicles was determined using our previously reported method based on quantitative $^{31}$P[1H] NMR spectroscopy.15 All experiments were performed in 90% H2O and 10% D2O using a Bruker Avance-400 spectrometer with a BBFO probe. A relaxation delay (D1) of 11 s was determined by inversion-recovery pulse sequence experiments. A phospholipid vesicle sample (890 μL in water) was mixed with 10 μL of Triton X-100 or rhamnolipid solution (to fully lyse the vesicles), and 100 μL of a triethylphosphine oxide (TPO) solution (100 mM in D2O) was added as an internal standard. Integrations for phospholipid peaks were performed relative to the phosphorus peak of TPO (δ~65 ppm). NMR acquisition parameters were as follows: PULPROG (pulse program)=zgig30, D1 (relaxation delay)=11 s, SW (sweep width)=405 ppm, O2P (transmitter frequency of f2 channel)=3.75 ppm, NS (number of scans)=64, DS (number of dummy scans)=4, LB (line broadening factor)=1.

Production of phospholipid vesicles with encapsulated calcein. Large unilamellar vesicles (LUVs) were produced by adapting a freeze-thaw and vesicle extrusion procedure (Mayer et al., 1986). Briefly, stock solutions of phospholipids (DOPC, DPPC, DPPE, or cholesterol) in chloroform were mixed to the desired lipid compositions (70 mol % DOPC/30 mol % cholesterol for S. aureus vesicles or 68 mol % DPPC, 30 mol % cholesterol, 2 mol % DPPE for P. aeruginosa vesicles), and the chloroform was removed using an N2 stream or rotary evaporation followed by drying for at least one hour under vacuum. Self-quenching solutions of calcein were prepared by combining calcein and PBS or a specially prepared calcein buffer (1 mM EDTA, 10 mM Trisbase, and 100 mM NaCl; pH 8) to a calcein concentration of 70 μM. The resulting solutions were titrated with 10 M aqueous NaOH until all calcein was dissolved and the solution reached pH 7.4 or pH 8 for PBS and the calcein buffer, respectively. The resulting calcein solutions were added to the dried phospholipid films (PBS for *S. aureus* formulations and the calcein buffer for the *P. aeruginosa* formulations) for a final lipid concentration of 5 mg/mL. The resulting lipid solutions were vortexed vigorously and briefly sonicated in a bath sonicator to form a turbid vesicle suspension. The vesicle suspensions were then freeze-thawed five times by alternately immersing them into an iPrOH/dry ice bath and a warm water bath (~60° C.). Vesicles prepared for continuous time-course experiments were passed at least 5 times through a 100 nm polycarbonate filter using a Mini-prep extruder. Vesicles prepared for the high-throughput screen were passed through the filter 3 times. The resulting vesicles were then separated from external, unloaded calcein using a hand-packed Sephadex-G50 size exclusion chromatography column. The concentration of phospholipid in the solution was quantified using $^{31}$P NMR (per the above protocol), and the phospholipid concentration was adjusted to 2 mM for unsaturated lipid solutions and 1 mM for saturated lipid solutions in their respective buffers. The resulting vesicles were characterized by dynamic light scattering and found to have a hydrodynamic diameter of ~150 nm (FIGS. 3A-3C), which agrees with previous reports describing vesicle production using a similar method (Lapinski et al., 2007).

Microtiter plate vesicle lysis assays. Portions of media (2 or 10 mL) were inoculated with individual bacterial colonies and allowed to shake overnight. From these overnight cultures, subcultures were prepared by diluting the cultures 1:50 (v/v) in fresh BHI for S. aureus or 1:100 (v/v) in fresh LB for *P. aeruginosa*. An aliquot of each subculture (178 μL) was added to 20 μL of vesicle suspension and 2 μL of compound solution (dissolved in DMSO at 100× working concentration) in a clear-bottomed, black 96-well microtiter plate (Corning 3904). For controls, DMSO (vehicle) or Triton X-100 (1% final concentration) was substituted for compound. Plate covers were coated with an aqueous solution of 0.05% Triton X-100 and 20% ethanol (Brewster, 2003) to prevent the accumulation of condensation. Plates were incubated in a Biotek Synergy 2 microplate reader running Gen5 1.05 software at 37° C. with shaking at the high-speed setting. Fluorescence (excitation 500 nm, emission 540 nm) and OD600 (absorbance at 600 nm) measurements were recorded every 15 minutes for 12 hours. All experiments were performed in technical triplicate in a single microtiter plate. Biological triplicates were then obtained over three days. GraphPad Prism software (v. 9) was used to generate curves and calculate standard error.

High-throughput screening and follow-up analysis protocols. Test compounds and positive control 1 were delivered in 2.5 nL aliquots of DMSO with an Echo 550 liquid handler (LabCyte Inc.) into black 384-well microtiter plates (Corning). All test compounds were tested at 10 μM; positive control 1 was tested at 250 nM. DMSO was used as a negative control. Overnight cultures (2 mL) of WT *S. aureus* (RN6390b) were grown at 37° C. with shaking at 200 rpm. These cultures were diluted 1:500 (v/v) in fresh BHI medium, at which point vesicle solutions were added to a final concentration of 1 mM phospholipid (as determined by $^{31}$P NMR analyses). This vesicle-cell mixture was then added to the 384-well microtiter plates with a Multidrop 384 liquid-dispensing robot (Thermo Scientific) for a total volume of 50 μL per well. Plates were incubated statically for ~24 hr at 37° C., at which point fluorescence (excitation 483, emission 530) and OD$_{600}$ (absorbance at 600 nm) measurements were made using a CLARIOstarR Plus microtiter plate reader (BMG Labtech) running MARS data analysis software. Scatter plots were generated using the Collaborative Drug Discovery Vault informatics platform. The dose-response experiment using the vesicle lysis assay was performed in a 384-well plate in technical duplicate with compound concentrations of 0.1, 0.25, 0.5, 1, 2.5, 5, 10, and 20 μM. Dose-response curves were generated using variable slope (4 parameter) non-linear regression analysis for compound inhibition using GraphPad Prism software (v. 9). Analysis of the QS modulatory activity of the HTS hits and 6 (savirin) was performed using the *S. aureus* YFP transcriptional reporter strain. HTS hits were purchased directly from Life Chemicals, Inc. DMSO stock solutions (10 mM) of each compound were prepared and stored at −20° C. Serial dilutions (1:3) were prepared from the stock solutions in DMSO, and 2 μL aliquots of the resulting dilutions were added to the wells of black 96-well microtiter plates (Corning). Overnight cultures of the *S. aureus* reporter strain (2 mL) were grown at 37° C. with shaking at 200 rpm. Cultures were diluted 1:50 (v/v) into fresh BHI medium, and 198 μL of this diluted culture were added to each well containing compound, for a total volume of 200 μL per well. All plates contained a vehicle control consisting of 2 μL of DMSO and 198 μL of culture and a media control consisting of 200 μL BHI. Plates were incubated for ~24 hours at 37° C. with shaking at 200 rpm. Fluorescence (excitation 510, emission 544) and OD$_{600}$ measurements were acquired with a PerkinElmer EnVision microtiter plate reader running Envision Manager software. Background fluorescence from BHI control was subtracted from raw fluorescence reads, OD$_{600}$ corrected, and finally normalized to vehicle control. Dose-response curves and IC$_{50}$ values were generated using 3-parameter non-linear regression analysis for compound inhibition using GraphPad Prism software (v. 9). All compounds were tested in technical triplicate with at least 3 biological replicates.

Example 1

Synthetic Lipid Vesicle Formulations

Simplified lipid vesicle formulations were identified that could respond selectively to membrane-lytic toxins but that would be more accessible and less time-consuming to prepare than prior formulations that required the use of polymerizable lipids or the use of specialized equipment (e.g., a UV oven). LUVs encapsulating the self-quenching fluorescent dye calcein were incubated with aliquots of lag phase wild-type (WT) or QS-deficient *S. aureus* and *P. aeruginosa* cultures (see Materials and General Methods for preparation and characterization of LUVs). These experiments were conducted in 96-well microtiter plates, and measurements of fluorescence were used to characterize vesicle stability and/or the release of encapsulated calcein over time. The *S. aureus* QS mutant used in these experiments (RN9222, see Table 1 (above) for bacterial strains and plasmids used in these Examples) lacks the AgrD and AgrB signal processing components of the agr system (FIG. 1A) and, thus, cannot produce its native AIP. The *P. aeruginosa* QS mutant used here (PAO-JG35) lacks two receptors for AHL signal recognition that are essential transcription factors for their respective regulons (i.e., LasR and RhlR, FIG. 1B). As such, these initial screens enabled us to identify lipid vesicle formulations that were stable, and did not release calcein, in the presence of the QS mutants (which cannot produce membrane-lytic toxins) and that were unstable, and did release calcein, in the presence of WT organisms (which can produce membrane-lytic compounds at high population densities).

Using this vesicle screening approach, we identified two LUV formulations. First, LUVs comprised of 70 mol % of the unsaturated zwitterionic lipid DOPC and 30 mol % cholesterol to respond selectively to WT strains of *S. aureus* (FIG. 2A). Second, formulations comprised of 68 mol % DPPC, 2 mol % DPPE, and 30 mol % cholesterol to respond selectively to WT strains of *P. aeruginosa* (FIG. 2B; this formulation was adapted from (Thet et al., 2013)). These two vesicle formulations were measured to be ~150 nm in diameter by dynamic light scattering (FIGS. 3A-3C), exhibited sufficient stability, with minimal dye leakage, in bacterial cultures containing the QSnull bacterial strains (and therefore the absence of lytic agents) for 12 hours, and were suitable for all other fundamental and discovery-oriented experiments described below. Control experiments demonstrated that the presence of these vesicles had minimal effects on cell growth over the course of these assays (FIGS. 4A-4D).

The results shown in FIGS. 2A-2B for WT strains versus QS mutants demonstrate that functional QS networks are required for substantial lysis of these vesicle formulations in the presence of either *S. aureus* or *P. aeruginosa*. Because the onset of QS is typically reported to occur at the middle to late log phase of bacterial growth (Novick, 2003, Schuster et al., 2003), these results also suggest that vesicle lysis correlates to the times at which quorum is reached in these bacterial cultures. Additional support for this view was provided by the results of experiments performed using WT bacteria containing QS transcriptional reporter plasmids (encoding yellow fluorescent protein (YFP) in the case of *S. aureus*, and green fluorescent protein (GFP) in the case of *P. aeruginosa*). The panels in FIGS. 2C-2D show comparisons of increases in normalized fluorescence for (i) vesicles incubated with WT strains and (ii) fluorescent protein production in cultures of the *S. aureus* (FIG. 2C) and *P. aeruginosa* (FIG. 2D) reporter strains. These results reveal the onset of vesicle leakage in experiments using WT bacteria to occur, in general, on time scales similar to those observed for fluorescent protein production (this correlation was more pronounced in the case of *S. aureus*; see FIG. 2C). We consider it likely that vesicle lysis was initiated in our WT cultures by the onset of production of membrane-lytic agents—i.e., PSMs (for *S. aureus*) and rhamnolipids (for *P. aeruginosa*). This conclusion is supported by past studies by Jenkins (Laabei et al., 2014a, Laabei et al., 2014b), and by the results of our own experiments in which solutions of authentic samples of either a representative PSM (PSMa3) or rhamnolipid were observed to lyse vesicles in a dosedependent manner (FIGS. 5A-5B).

Example 2

Validation of Assay Method Using Responsive Vesicles and Known Inhibitors of QS

We conducted a series of experiments to validate the two responsive vesicle formulations identified above as platforms for the identification of inhibitors of QS by adding known QS modulators (structures shown in FIGS. 6A-6B) to cultures of *S. aureus* and *P. aeruginosa* in the presence of vesicles. For experiments with *S. aureus*, we selected the native AIP as an activator, and three inhibitors of the two-component AgrC/AgrA signaling system (FIG. 1A). Two of these inhibitors (compounds 1 and 5), which we reported on previously (Tal-Gan et al., 2013, Vasquez and Blackwell, 2019), are macrocyclic, peptide-based molecules that likely function via competitive inhibition of the AIP ligand:AgrC receptor binding interaction. The third inhibitor, the small molecule 6 (savirin, (Sully et al., 2014)) has been shown to inhibit the agr system in *S. aureus* via binding and ostensible inactivation of AgrA, the response regulator of the transmembrane histidine kinase, AgrC. For experiments with *P. aeruginosa*, we used the native ligands of three of its key QS transcriptional regulators LasR, RhlR, and PqsR (FIG. 1B)—i.e., the activators N-(3-oxo-dodecanoyl)-L-homoserine lactone (OdDHL), N-butyryl-Lhomoserine lactone (BBL), and the *Pseudomonas* quinolone signal (PQS), respectively—as well as the LasR antagonist 7 (V-06-018, (Muh et al., 2006b)) the potent PqsR antagonist 8 (M64, (Starkey et al., 2014)) and the non-native AHL-derived RhlR activator 9 (Eibergen et al., 2015).

We incubated bacterial cultures containing calcein-loaded vesicles with aliquots of each of these compounds at concentrations needed for near-maximal inhibition or activation (as reported in previous studies) and monitored changes in fluorescence of the cultures over 12 hours (FIGS. 7A-7D). We also conducted parallel control experiments using a QS mutant strain to determine whether observed changes in vesicle permeabilization were a result of bacterial production of membrane-lytic toxins and not the potential surface/membrane activity of these QS inhibitors. For experiments using *S. aureus*, inhibitors 1 and 6 wholly abrogated vesicle lysis (FIG. 7A; blue and purple curves), consistent with their ability to nearly completely quench agr activity. The addition of inhibitor 5 suppressed dye release, relative to vehicle controls containing no inhibitor, over 12 hours, yet we observed a steady increase in fluorescence during the course of these experiments (red curve), suggesting that agr activity was not completely blocked under the conditions used here. The reasons for this reduced activity for 5 are not completely understood. It is possible that this result may reflect an intrinsic inability of this compound to fully inhibit the agr system, with a basal amount of agr activity allowing for low levels of PSM to accumulate and affect low levels of membrane disruption. This result could also, however, arise from the sequestration of this inhibitor resulting from interactions with the vesicles, aggregation, and/or degradation, each of which would reduce in situ concentrations and affect inhibitory activity.

Turning to a QS agonist, we observed that the exogenous addition of native AIP triggered calcein leakage approximately two hours earlier in the WT organism relative to the vehicle control (FIG. 7B), even though the culture remained in the lag/early exponential phase of growth (FIG. 8B). This result is consistent with the production of membrane-lytic toxins in sub-quorate populations of bacteria treated with strong agr agonists (i.e., prematurely forcing group behavior) and suggests that temporal dynamics associated with vesicle leakage could also be used to screen for and identify new agonists of QS in *S. aureus*. Finally, none of the compounds investigated here affected calcein leakage when incubated with the agr-null strain (i.e., QS mutant, FIG. 8A), confirming that the results shown in FIGS. 7A-7B result from compound/agr system interactions and not any other direct physicochemical influence of these compounds on membrane permeability. The native AIP and peptide analogs 1 and 5 had minimal impact on cell growth; small molecule 6 showed some effects on growth at later time points (FIGS. 8B, 8C).

The overall trends in experiments using *P. aeruginosa* and our vesicle lysis assay were similar to those observed above;

however, the influence of QS inhibitors used in this organism on calcein leakage was generally more complex, and thus more difficult to interpret, than those observed in *S. aureus*. Inspection of the results in FIG. 7C reveals that LasR antagonist 7 and PqsR antagonist 8 (FIGS. 6A-6B) significantly delayed vesicle lysis by approximately two hours relative to vehicle controls, but that, in both cases, fluorescence continued to increase over the course of 12 hours. Interestingly, the influence of the addition of QS agonists varied based on their target receptors in this organism. For example, the native LasR agonist OdDHL and PqsR agonist PQS (FIGS. 6A-6B) had no observable influence on levels of fluorescence (FIG. 7D; red and green curves), in contrast to the addition of a QS agonist in the presence of *S. aureus* (FIG. 7B). However, treatment with the native RhlR agonist BHL and non-native RhlR agonist 9 resulted in an earlier onset of dye leakage (FIG. 7D; pink and purple curves). We note that both the Las and Pqs systems play roles in activation of the Rhl system, and that Rhl plays a key role in the regulation of rhamnolipid production in *P. aeruginosa* (Schuster and Greenberg, 2008). These results are thus consistent with past reports from our group on the interplay of the Las-Rhl-Pqs signaling network and its impact on the production of rhamnolipids (Welsh et al., 2015). Finally, we note that the native QS signaling molecules and compounds 7-9 had negligible effects on either calcein leakage (in the presence of QS mutants, FIG. 9A) or bacterial growth (FIGS. 9B and 9C), although compound 7 was observed to inhibit growth mildly at later time points.

We conducted an additional series of experiments to characterize the sensitivity of vesicle lysis in bacterial cultures to changes in the concentrations and potencies of added QS inhibitors. High sensitivity to these differences would increase the utility of this assay for a range of screening applications. For these experiments, we focused our efforts on characterization in cultures of *S. aureus*, as we had ready access to a suite of structurally related agr inhibitors with well-understood activity profiles previously identified by our group (i.e., 1-4; FIGS. 6A-6B) (Tal-Gan et al., 2013, Tal-Gan et al., 2016, Vasquez and Blackwell, 2019). We also reasoned that the results for this organism would be easier to interpret than those arising from experiments with *P. aeruginosa* in view of its more complex and inter-regulated QS network (vide supra). Calceinloaded vesicles were incubated with WT *S. aureus* and 3-fold dilutions of QS inhibitor 1, starting at a concentration of 100 nM. Increasing concentrations of 1 were observed to lead to increases in the times required for the onset of calcein leakage (FIG. 10A). We also examined whether vesicle leakage could be used to identify differences in the potencies of the four structurally similar agr inhibitors (1-4). For these experiments, all compounds were tested at equivalent concentrations of 100 nM. Inspection of FIG. 10B reveals the more potent inhibitors 1 and 3 completely prevent calcein leakage, whereas their less potent amide-bridged analogs 2 and 4 resulted only in a delayed response. At 12 hr, we observed a clear correlation between compound potency (as determined previously using cell-based transcriptional reporter assays) and fluorescence as a measure of vesicle lysis (FIG. 10C).

When combined, the results of the experiments above demonstrate that the presence (or absence) of calcein leakage can be used to identify the presence (or absence) of inhibitors or agonists of QS in cultures of *S. aureus* and *P. aeruginosa*. In addition, the vesicle lysis assay can be used to report the relative amounts and potencies of QS inhibitors. Our results support the view that the ability of this materials platform to discriminate and report on QS is a result of the sensitivity of calcein leakage to the production of membrane-lytic toxins in these organisms, and suggest that the timing and the magnitude of calcein leakage may also convey useful information related to potency or other dynamics in these systems. Overall, the impacts of added QS inhibitors and activators on calcein leakage are more straightforward to interpret in cultures of *S. aureus* (at least under the conditions evaluated in this work) relative to *P. aeruginosa*. However, decreases in calcein fluorescence of the cultures induced by QS inhibitors in the latter are significant and can still be observed in FIGS. 7A-7D.

Example 3

A High-Throughput Screen Identifies Novel and Potent Small-Molecule Inhibitors of agr-type QS We conducted a final series of experiments to explore the feasibility of using the vesicle leakage assay described above as a platform for the high-throughput screening and identification of new small-molecule inhibitors of agr-type QS in *S. aureus*. For these experiments, we used WT *S. aureus* and the 70% DOPC/30% cholesterol vesicles characterized above, and the assay was re-optimized for use in an automated, 384-well microtiter plate format (see Methods). We selected agr inhibitor 1 (FIGS. 6A-6D) as a positive control for these studies and screened a commercially available small molecule library of 25,280 compounds (at concentrations of 10 µM; see General Methods above). Each microtiter plate contained positive (250 nM 1) and negative (DMSO vehicle) controls in addition to 320 wells containing test compounds. After the addition of an aliquot of a vesicle/cell mixture, plates were incubated statically for 24 hr at 37° C., at which point fluorescence and optical density readings were acquired.

These high-throughput assays identified 92 compounds that resulted in <80% fluorescence emission relative to the vehicle control (FIG. 11A). Subsequent dose-response analysis of these initial hits using the vesicle leakage assay identified five compounds with strong activity profiles, with three compounds able to completely block vesicle lysis at concentrations >10 µM (FIG. 11B). The abilities of these lead hit compounds to target agr in *S. aureus* was evaluated using an agr transcriptional reporter assay (FIG. 11C), revealing two compounds (the pyrazolopyrimidine 10 and thiazolopyridine derivative 11, FIG. 11D) as near maximal agr inhibitors. We note that compounds 10 and 11 are approximately 5-10 times more potent than compound 6 in the reporter assay (10 ($IC_{50}$=0.5 µM) and 11 ($IC_{50}$=0.7 µM) vs. 6 ($IC_{50}$=5.5 µM)), which is one of the strongest small-molecule inhibitors of QS reported to date in *S. aureus* (Sully et al., 2014), and that these two compounds do not inhibit cellular growth.

Both 10 and 11 are low molecular weight (MW<500 g/mol), readily soluble in DMSO and aqueous solutions, contain no obvious reactive sites that could potentially lead to compound degradation, and are readily amenable to synthetic modification. We note that while compound 10 and its analogs have been reported to be agonists of the human apelin receptor (Smith, 2019), a G protein-coupled receptor unrelated to the agr system, neither compound 10 nor 11 has previously been reported to influence bacterial QS.

Figure 12:
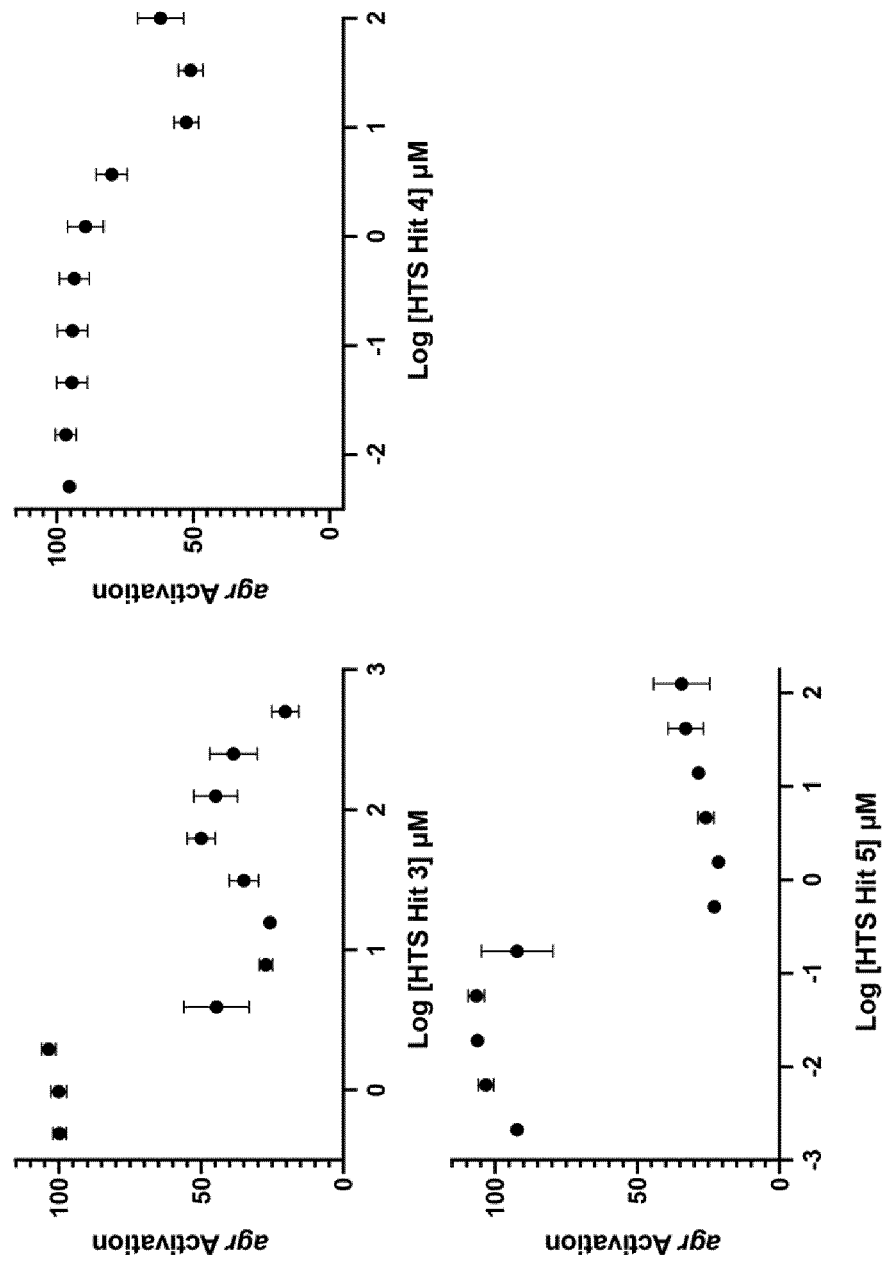
FIG. 12 shows dose-response agr inhibition data for high-throughput screen (HTS) hit compounds 3-5 in the *S. aureus* agr reporter strain containing a YFP QS plasmid (pDB59). Data points represent the mean of all replicates (n=9). Error bars=SEM.

The potency, efficacy, and small-molecule nature of compounds 10 and 11 make them valuable additions to the available toolbox of agr inhibitors. Additional characterization of these compounds, including delineating their mechanisms of agr inhibition and exploration of potential structure-activity relationships that could be useful for the generation of new synthetic derivatives, is currently underway and will be reported in due course. While we immediately recognized and have focused here on the utility of 10 and 11, we note that three additional hit compounds (HTS hits 3-5, FIG. 11B) were active in our cell-based agr transcriptional reporter assay (albeit not to the extent of 10 and 11; FIG. 12), and the activity profiles of these compounds also warrant additional scrutiny. In the context of this current work, however, the identification of 10 and 11 as potent, small-molecule based agr inhibitors underscores the utility of our vesicle leakage assay as an accessible and high-throughput platform for the discovery of novel QSMs.

Example 4

New Inhibitors of agr-Type QS in S. aureus

A series of compounds based on Formula I and shown in the Table 2 below were prepared according to standard methods in the art (e.g., condensing 1,3-dicarbonyl compounds with 3-aminopyrazoles using heat and/or catalyst, followed by, e.g., by a Suzuki reaction to install an aromatic group optionally bearing $R^3$). The compounds of Table 2 each exhibited MS and/or other analytical data consistent with structures depicted. The compounds were assayed as described in Example 3. Assay results are also shown in the Table 2.

TABLE 2

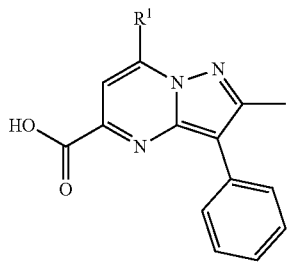

| Compound No. | $R^1$ | $IC_{50}$ (µM) |
|---|---|---|
| 10 | Isopropyl | 1.22 |
| 12 | n-Propyl | 2.58 |
| 13 | Cyclopropyl | 3.35 |
| 14 | Cyclobutyl | 0.98 |
| 15 | Ethyl | 7.67 |
| 16 | Cyclopentyl | 0.84 |
| 17 | t-Butyl | 0.48 |
| 18 | Methyl | |
| 19 | OH/=O | |

REFERENCES

Boursier, M. E., Moore, J. D., Heitman, K. M., Shepardson-Fungairino, S. P., Combs, J. B., Koenig, L. C., Shin, D., Brown, E. C., Nagaraj an, R. & Blackwell, H. E. 2018. Structure function analyses of the N-butanoyl L-homoserine lactone quorum-sensing signal define features critical to activity in RhlR. ACS Chem. Biol., 13, 2655-2662.

Brewster, J. D. 2003. A simple micro-growth assay for enumerating bacteria. J. Microbiol. Methods, 53, 77-86.

De Kievit, T. R.; Gillis, R.; Marx, S.; Brown, C.; Iglewski, B. H. Quorum-sensing genes in Pseudomonas aeruginosa biofilms: their role and expression patterns. Appl. Environ. Microbiol. 2001, 67, 1865-1873.

Eibergen, N. R., Moore, J. D., Mattmann, M. E. & Blackwell, H. 2015. Potent and selective modulation of the RhlR quorum sensing receptor by using non-native ligands: An emerging target for virulence control in Pseudomonas aeruginosa. ChemBioChem, 16, 2348-2356.

Gerdt, J. P.; Blackwell, H. E. Competition studies confirm two major barriers that can preclude the spread of resistance to quorum-sensing inhibitors in bacteria. ACS Chem. Biol. 2014, 9, 2291-2299.

Hodgkinson, J. T., Galloway, W. R. J. D., Casoli, M., Keane, H., Su, X., Salmond, G. P. C., Welch, M. & Spring, D. R. 2011. Robust routes for the synthesis of N-acylated-Lhomoserine lactone (AHL) quorum sensing molecules with high levels of enantiomeric purity. Tet. Lett., 52, 3291-3294.

Kirchdoerfer, R. N.; Garner, A. L.; Flack, C. E.; Mee, J. M.; Horswill, A. R.; Janda, K. D.; Kaufmann, G. F.; Wilson, I. A. Structural basis for ligand recognition and discrimination of a quorum-quenching antibody. J. Biol. Chem. 2011, 286, 17351-17358.

Laabei, M., Jamieson, W. D., Lewis, S. E., Diggle, S. P. & Jenkins, A. T. A. 2014a. A new assay for rhamnolipid detection-important virulence factors of Pseudomonas aeruginosa. Appl. Microbiol. Biotechnol., 98, 7199-7209.

Laabei, M., Jamieson, W. D., Massey, R. C. & Jenkins, A. T. A. 2014b. Staphylococcus aureus interaction with phospholipid vesicles—a new method to accurately determine accessory gene regulator (agr) activity. PLoS ONE, 9, e87270.

Lapinski, M. M., Castro-Forero, A., Greiner, A. J., Ofoli, R. Y. & Blanchard, G. J. 2007. Comparison of liposomes formed by sonication and extrusion: Rotational and translational diffusion of an embedded chromophore. Langmuir, 23, 11677-11683.

Loureiro-Ferreira, N., Rodrigues, J., Brito, R. M. M 2008. NMR structure of delta-toxin from Staphylococcus aureus in CD3OH.

Lyon, G. J., Mayville, P., Muir, T. W. & Novick, R. P. 2000. Rational design of a global inhibitor of the virulence response in Staphylococcus aureus, based in part on localization of the site of inhibition to the receptor-histidine kinase, AgrC. Proc. Natl. Acad. Sci. U. S. A., 97, 13330-13335.

Manson, D. E., O'Reilly, M. C., Nyffeler, K. E. & Blackwell, H. E. 2020. Design, synthesis, and biochemical characterization of non-native antagonists of the Pseudomonas aeruginosa quorum sensing receptor LasR with nanomolar IC50 values. ACS Infect. Dis., 6, 649-661.

Mayer, L. D., Hope, M. J. & Cullis, P. R. 1986. Vesicles of variable sizes produced by a rapid extrusion procedure. Biochim. Biophys. Acta, 858, 161-168.

Muh, U., Schuster, M., Heim, R., Singh, A., Olson, E. R. & Greenberg, E. P. 2006b. Novel Pseudomonas aeruginosa quorum-sensing inhibitors identified in an ultra-hight-hroughput screen. Antimicrob. Agents Chemother., 50, 3674-3679.

Novick, R. P. Properties of a cryptic high-frequency transducing phage in Staphylococcus aureus. Virology 1967, 33, 155-166.

Novick, R. P.; Ross, H. F.; Projan, S. J.; Kornblum, J.; Kreiswirth, B. N.; Moghazeh, S. Synthesis of Staphylococcal virulence factors is controlled by a regulator RNA molecule. EMBO J. 1993, 12, 3967-3975.

Novick, R. P. 2003. Autoinduction and signal transduction in the regulation of staphylococcal virulence. *Mol. Microbiol.*, 48, 1429-1449. 30

Schuster, M. & Greenberg, E. P. 2008. LuxR-type proteins in *Pseuodomonas aeruginosa* quorum sensing: Distinct mechanisms with global implications. *Chemical communication among bacteria.* Washington, D.C.: ASM Press.

Schuster, M., Lostroh, C. P., Ogi, T. & Greenberg, E. P. 2003. Identification, timing, and signal specificity of *Pseudomonas aeruginosa* quorum-controlled genes: A transcriptome analysis. *J. Bacteriol.*, 185, 2066-2079.

Smith, L. H., Pinkerton, A. B., Hershberger, P. M., Maloney, P., Mcanally, D. 2019. *Apelin Receptor Agonists and Methods of Use Thereof.* WO/2019/032720

Starkey, M., Lepine, F., Maura, D., Bandyopadhaya, A., Lesic, B., He, J., Kitao, T., Righi, V., Milot, S., Tzika, A. & Rahme, L. 2014. Identification of anti-virulence compounds that disrupt quorum-sensing regulated acute and persistent pathogenicity. *PLoS Pathog.*, 10, e1004321.

Sully, E. K., Malachowa, N., Elmore, B. O., Alexander, S. M., Femling, J. K., Gray, B. M., Deleo, F. R., Otto, M., Cheung, A. L., Edwards, B. S., Sklar, L. A., Horswill, A. R., Hall, P. R. & Gresham, H. D. 2014. Selective chemical inhibition of agr quorum sensing in *Staphylococcus aureus* promotes host defense with minimal impact on resistance. *PLoS Pathog.*, 10, e1004174.

Tal-Gan, Y., Ivancic, M., Cornilescu, G., Yang, T. & Blackwell, H. E. 2016. Highly stable, midebridged autoinducing peptide analogues that strongly inhibit the AgrC quorum sensing receptor in *Staphylococcus aureus*. *Angew. Chem. Int. Ed.*, 55, 8913-8917.

Tal-Gan, Y., Stacy, D. M., Foegen, M. K., Koenig, D. W. & Blackwell, H. E. 2013. Highly potent inhibitors of quorum sensing in *Staphylococcus aureus* revealed through a systematic synthetic study of the group-III autoinducing peptide. *J. Am. Chem. Soc.*, 135, 7869-7882.

Thet, N. T., Hong, S. H., Marshall, S., Laabei, M., Toby, A. & Jenkins, A. 2013. Visible, colorimetric dissemination between pathogenic strains of *Staphylococcus aureus* and 31 *Pseudomonas aeruginosa* using fluorescent dye containing lipid vesicles. *Biosens. Bioelectron.*, 41, 538-543.

Vasquez, J. K. & Blackwell, H. E. 2019. Simplified autoinducing peptide mimetics with single nanomolar activity against the *Staphylococcus aureus* AgrC quorum sensing receptor. *ACS Infect. Dis.*, 5, 484-492.

Welsh, M. A. & Blackwell, H. E. 2016a. Chemical genetics reveals environment-specific roles for quorum sensing circuits in *Pseudomonas aeruginosa*. *Cell Chem. Biol.*, 23, 361-369.

Welsh, M. A., Eibergen, N. R., Moore, J. D. & Blackwell, H. E. 2015. Small molecule disruption of quorum sensing cross-regulation in *Pseudomonas aeruginosa* causes major and unexpected alterations to virulence phenotypes. *J. Am. Chem. Soc.*, 137, 1510-1519.

Yarwood, J. M.; Bartels, D. J.; Volper, E. M.; Greenberg, E. P. 2004. Quorum sensing in *Staphylococcus aureus* biofilms. *J. Bacteriol.*, 186, 1838-1850.

EQUIVALENTS

While certain embodiments have been illustrated and described, a person with ordinary skill in the art, after reading the foregoing specification, can effect changes, substitutions of equivalents and other types of alterations to the conjugates and micelles of the present technology or derivatives, prodrugs, or pharmaceutical compositions thereof as set forth herein. Each aspect and embodiment described above can also have included or incorporated therewith such variations or aspects as disclosed in regard to any or all of the other aspects and embodiments.

The present technology is also not to be limited in terms of the particular aspects described herein, which are intended as single illustrations of individual aspects of the present technology. Many modifications and variations of this present technology can be made without departing from its spirit and scope, as will be apparent to those skilled in the art. Functionally equivalent methods within the scope of the present technology, in addition to those enumerated herein, will be apparent to those skilled in the art from the foregoing descriptions. Such modifications and variations are intended to fall within the scope of the appended claims. It is to be understood that this present technology is not limited to particular methods, conjugates, reagents, compounds, compositions, labeled compounds or biological systems, which can, of course, vary. It is also to be understood that the terminology used herein is for the purpose of describing particular aspects only, and is not intended to be limiting. Thus, it is intended that the specification be considered as exemplary only with the breadth, scope and spirit of the present technology indicated only by the appended claims, definitions therein and any equivalents thereof The embodiments, illustratively described herein may suitably be practiced in the absence of any element or elements, limitation or limitations, not specifically disclosed herein. Thus, for example, the terms "comprising," "including," "containing," etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the claimed technology. Additionally, the phrase "consisting essentially of" will be understood to include those elements specifically recited and those additional elements that do not materially affect the basic and novel characteristics of the claimed technology. The phrase "consisting of" excludes any element not specified.

In addition, where features or aspects of the disclosure are described in terms of Markush groups, those skilled in the art will recognize that the disclosure is also thereby described in terms of any individual member or subgroup of members of the Markush group. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like, include the number recited and refer to ranges which can be subsequently broken down into subranges as discussed above. Finally, as will be understood by one skilled in the art, a range includes each individual member.

All publications, patent applications, issued patents, and other documents (for example, journals, articles and/or textbooks) referred to in this specification are herein incorporated by reference as if each individual publication, patent application, issued patent, or other document was specifically and individually indicated to be incorporated by reference in its entirety. Definitions that are contained in text incorporated by reference are excluded to the extent that they contradict definitions in this disclosure.

Other embodiments are set forth in the following claims, along with the full scope of equivalents to which such claims are entitled.

What is claimed is:

1. A compound having the structure of Formula I:

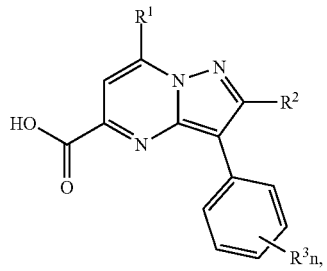

and/or a pharmaceutically acceptable salt thereof, wherein
$R^1$ is OH or its oxo tautomer;
$R^2$ is H, halogen, OH, $NO_2$, or a substituted or unsubstituted alkyl, cycloalkyl or cycloalkylalkyl group;
$R^3$ is a halogen, CN, $NO_2$, or a substituted or unsubstituted alkyl, cycloalkyl, or cycloalkylalkyl group; and
n is 0, 1, 2, 3, 4 or 5.

2. A method of inhibiting quorum sensing by bacteria comprising administering an effective amount of a compound of Formula I to a subject in need thereof:

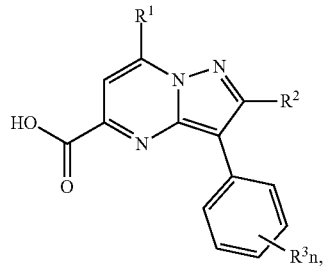

and/or a pharmaceutically acceptable salt thereof, wherein
$R^1$ is OH or its oxo tautomer;
$R^2$ is H, halogen, OH, CN, $NO_2$, or a substituted or unsubstituted alkyl, cycloalkyl or cycloalkylalkyl group;
$R^3$ is a halogen, CN, $NO_2$, or a substituted or unsubstituted alkyl, cycloalkyl, or cycloalkylalkyl group; and
n is 0, 1, 2, 3, 4 or 5.

3. The method of claim 2, wherein $R^1$ is a substituted or unsubstituted alkyl or cycloalkyl, group.

4. The method of claim 3, wherein $R^1$ is an unsubstituted $C_{1-6}$ alkyl group or an unsubstituted $C_{3-6}$ cycloalkyl group.

5. The method of claim 4, wherein $R^1$ is a methyl, ethyl, isopropyl, n-propyl, t-butyl, cyclopropyl, cyclobutyl, or cyclopentyl group.

6. The method of claim 2, wherein $R^2$ is halogen, OH, $NO_2$, or a substituted or unsubstituted alkyl or cycloalkyl group.

7. The method of claim 6, wherein $R^2$ is fluoro, chloro, OH, $NO_2$, or an unsubstituted methyl, ethyl, isopropyl, cyclopropyl, or cyclobutyl group.

8. The method of claim 2, wherein $R^3$ is halogen, $NO_2$, or a substituted or unsubstituted alkyl or cycloalkyl group.

9. The method of claim 8, wherein $R^3$ is F, Cl, NO2, or an unsubstituted $C_{1-6}$ alkyl group.

10. A pharmaceutical composition comprising a compound of claim 1 and a pharmaceutically acceptable carrier and/or excipient.

11. A method of treating a bacterial infection in a subject comprising administering an effective amount of a compound of claim 1, wherein the bacterial infection is caused by bacteria that release a membrane-lytic toxin.

12. The method of claim 11, wherein the bacteria are selected from the group consisting of *Bacillus, Burkholderia, Enterococcus, Escherichia, Listeria, Pseudomonas, Staphylococcus, Streptococcus*, and *Vibrio*.

13. The method of claim 12, wherein the bacteria are selected from the group consisting of *B. anthracis, B. cereus, E. faecalis, E. coli, L. monocytogenes, S. aureus, S. epidermidis, S. pyogenes, P. aeruginosa, P. chlororaphis, P. plantarii, P. putida, P. fluorescens*, and *B. thailandensis*.

14. The method of claim 12, wherein the bacteria are *S. aureus* or *P. aeruginosa*.

* * * * *